US011649271B2

(12) United States Patent
Monnet et al.

(10) Patent No.: US 11,649,271 B2
(45) Date of Patent: May 16, 2023

(54) FC MUTANTS WITH MODIFIED FUNCTIONAL ACTIVITY

(71) Applicant: LABORATOIRE FRANCAIS DU FRACTIONNEMENT ET DES BIOTECHNOLOGIES, Les Ulis (FR)

(72) Inventors: Celine Monnet, Lambersart (FR); Philippe Mondon, Neuve Chapelle (FR); Alexandre Fontayne, La Madeleine (FR); Christophe De Romeuf, Lambersart (FR)

(73) Assignee: LABORATOIRE FRANÇ-AIS DU FRACTIONNEMENT ET DES BIOTECHNOLOGIES, Puteaux (FR)

( * ) Notice: Subject to any disclaimer, the term of this patent is extended or adjusted under 35 U.S.C. 154(b) by 469 days.

(21) Appl. No.: 15/554,022

(22) PCT Filed: May 6, 2016

(86) PCT No.: PCT/FR2016/051068
§ 371 (c)(1),
(2) Date: Aug. 28, 2017

(87) PCT Pub. No.: WO2016/177984
PCT Pub. Date: Nov. 10, 2016

(65) Prior Publication Data
US 2018/0030111 A1    Feb. 1, 2018

(30) Foreign Application Priority Data
May 7, 2015 (FR) ..................... 15 54101

(51) Int. Cl.
*C07K 14/735*   (2006.01)
*C07K 16/28*    (2006.01)
*C07K 16/00*    (2006.01)
*A61K 39/395*   (2006.01)
*G01N 33/53*    (2006.01)
*G01N 33/68*    (2006.01)

(52) U.S. Cl.
CPC ...... *C07K 14/70535* (2013.01); *A61K 39/395* (2013.01); *C07K 16/00* (2013.01); *C07K 16/2803* (2013.01); *C07K 16/2887* (2013.01); *G01N 33/53* (2013.01); *G01N 33/6857* (2013.01); *C07K 2317/21* (2013.01); *C07K 2317/24* (2013.01); *C07K 2317/41* (2013.01); *C07K 2317/524* (2013.01); *C07K 2317/526* (2013.01); *C07K 2317/53* (2013.01); *C07K 2317/71* (2013.01); *C07K 2317/72* (2013.01); *C07K 2317/732* (2013.01); *C07K 2317/734* (2013.01); *C07K 2319/30* (2013.01)

(58) Field of Classification Search
None
See application file for complete search history.

(56) References Cited

U.S. PATENT DOCUMENTS

| 7,355,008 B2* | 4/2008 | Stavenhagen ........ C07K 16/005 |
| | | 530/387.1 |
| 2007/0015239 A1 | 1/2007 | Bihoreau et al. |
| 2012/0009188 A1* | 1/2012 | Behrens ................. C07K 16/00 |
| | | 424/133.1 |
| 2014/0342404 A1 | 11/2014 | Presta |

FOREIGN PATENT DOCUMENTS

| CN | 102405231 A | 4/2012 |
| FR | 3 012 453 A1 | 5/2015 |
| JP | 2012-524522 A | 10/2012 |
| JP | 2018-515446 A | 6/2018 |
| WO | 2005/040221 A1 | 5/2005 |
| WO | 2010/106180 A2 | 9/2010 |
| WO | 2011/044368 A1 | 4/2011 |

OTHER PUBLICATIONS

Vidarsson et al (F. Immu., 5(520):1-17, 2014).*
Shields R L et al.: "High resolution mapping of the binding site on human IgG1 for FcgammaRI, FcgammaRII, FcgammaRIII, and FcRn and design of IgG1 variants with improved binding to the FcgammaR", Journal of Biological Chemistry, American Society for Biochemistry and Molecular Biology, US, vol. 276, No. 9, Mar. 2, 2001 (Mar. 2, 2001), pp. 6591-6604, XP002271092, ISSN: 0021-9258.
International Search Report, dated Sep. 30, 2016, from corresponding PCT/FR2016/051068 application.
Search Report issued in French Patent Application No. 1554101 dated Sep. 3, 2020 with English machine translation provided.
Idusogie, E. et al., "Engineered Antibodies with Increased Activity to Recruit Complement," The Journal of Immunology, 2001, pp. 2571-2575.

* cited by examiner

*Primary Examiner* — Brad Duffy
(74) *Attorney, Agent, or Firm* — Nixon & Vanderhye

(57) ABSTRACT

Disclosed is to a polypeptide including a mutated Fc region and having functional activity, mediated by the Fc region, that is modified compared with that of a parent polypeptide. The Fc region includes at least one combination of 2 mutations, the combination being selected from among one mutation selected from among a first set of mutations, and at least one mutation selected from among a second set of mutations, and provided that mutation (i) does not take place on the same amino acid as mutation (ii). Also disclosed are use of the polypeptide, compositions including the same, and methods for preparing the polypeptide.

24 Claims, No Drawings
Specification includes a Sequence Listing.

FC MUTANTS WITH MODIFIED FUNCTIONAL ACTIVITY

The present invention relates to a polypeptide comprising a mutated Fc region and having functional activity, mediated by the Fc region, that is modified compared with that of a parent polypeptide.

An antibody is formed of a tetramer of heavy and light chains. The two light chains are identical, and the two heavy chains are identical and linked by disulfide bridges. There are five types of heavy chains (alpha, gamma, delta, epsilon, mu) which determine immunoglobulin classes (IgA, IgG, IgD, IgE, IgM). The light chain group comprises two sub-types: lambda and kappa.

IgGs are soluble antibodies which can be found in the blood and other body fluids. IgG is a Y-shaped glycoprotein with an approximate molecular weight of 150 kDa, composed of two heavy chains and two light chains. Each chain is characterized by a constant region and a variable region. The two carboxy-terminal domains of the heavy chains form the Fc fragment, whilst the amino-terminal domains of the heavy and light chains recognize the antigen and are known as the Fab fragment.

Fc fusion proteins are created by a combination of an antibody Fc fragment with a protein domain which provides specificity for a given therapeutic target. Examples are combinations of the Fc fragment with all types of therapeutic proteins or fragments thereof.

Therapeutic antibodies and Fc fusion proteins are currently used to treat various diseases such as rheumatoid polyarthritis, psoriasis, multiple sclerosis and numerous forms of cancer. Therapeutic antibodies may be monoclonal or polyclonal antibodies. Monoclonal antibodies are obtained from a unique antibody cell production line which exhibits identical specificity for a single antigen. Therapeutic Fc fusion proteins are used or developed as medicinal products against autoimmune diseases, e.g. etanercept (Enbrel by Amgen, a TNF receptor linked to an Fc fragment) or Alefacept (Amevive by Biogen Idec: LFA-3 linked to the Fc portion of human IgG1).

So that antibodies and Fc fusion proteins are able to exert their effects, the Fc fragment must have the best activity possible (e.g. antibody-dependent cell cytotoxicity, complement-dependent cytotoxicity or antibody-dependent cell phagocytosis) i.e. it is optimised. Said optimisation would allow a protein to be obtained having improved activity and/or efficacy and/or reduced side effects.

The Applicant has henceforth developed particular Fc fragments having improved activity. These fragments can be used for therapy to impart improved efficacy to a product containing the same.

The present invention therefore provides a variant of a parent polypeptide, having optimised properties related to the functional activity mediated by the Fc region.

The present invention relates to a polypeptide comprising a mutated Fc region and having functional activity, mediated by the Fc region, that is modified in comparison with that of a parent polypeptide, said Fc region comprising at least one mutation selected from among: G316D, K326E, N315D, N361H, P396L, T350A, V284L, V323I, P352S, A378V, Y436H, V266M, N421T, G385R, K326T, H435R, K447N, N434K, K334N, V397M, E283G, A378T, F423L, A431V, F423S, N325S, P343S, K290E, S375R, F405V, K322E, K340E, N389S, F243I, T307P, N389T, S442F, K248E, Y349H, N286I, T359A, S383R, K334R, T394P, V259A, T393A, P352L, Q418P, V302A, L398P, F423P, S442P, V363I, S383N, S254F, K320E, G402D, I253F, V284A, A431T, N315H, Y319H, C226Y, F405L, T393I, N434S, R255W, A287T, N286Y, A231V, K274R, V308G, K414R, M428T, E345G, F243L, P247T, Q362R, S440N, Y278H, D312G, V262A, V305A, K246R, V308I, E380G, N276S, K439Q, S267G, F423Y, A231T, K320R, L410R, K320M, V412M, T307N, T366A, P230S, Y349S, A339T, K246E, K274E, A231P, I336T, S298N, L234P, S267N, V263A, E333G, V308A, K439R, K392R, S440G, V397I, I336V, Y373D, K288E, L309P, P227S, V379A, K288R, K320T, V282A, I377T, N421S and C261R, the numbering being that of the EU index or Kabat equivalent.

Said polypeptide is called <<polypeptide of the invention>> in the present application.

More specifically, the present invention relates to a polypeptide comprising a mutated Fc region and having functional activity, mediated by the Fc region, that is modified in comparison with that of a parent polypeptide, said Fc region comprising at least one combination of 2 mutations, said combination being selected from among:

(i) one mutation selected from among 307N, 326E, 326T, 334N, 334R, 352L, 378V, 378T, 394P, 396L, 397M and 421T;

(ii) at least one mutation selected from among 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N, the numbering being that of the EU index or Kabat equivalent, provided that mutation (i) does not take place on the same amino acid as mutation (ii).

Preferably, mutation (i) is selected from among 378V, 396L and 397M. Preferably, the polypeptide also comprises a mutation selected from among 248E, 326T, 333G and 423Y.

Preferably, mutation (ii) of the invention is selected from among 226Y, 227S, 230S, 231V, 234P, 243I, 243L, 246R, 246E, 247T, 248E, 253F, 254F, 255W, 259A, 261R, 262A, 263A, 266M, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378T, 379A, 380G, 383R, 385R, 389S, 389T, 392R, 393A, 393I, 394P, 396L, 397I, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N.

Throughout this present application, the numbering of the residues in the Fc region is the numbering of the immunoglobin heavy chain in accordance with the EU Index or equivalent in Kabat et al. (Sequences of Proteins of Immunological Interest, 5$^{th}$ Ed. Public Health Service, National Institutes of Health, Bethesda, Md., 1991). The expression <<EU Index or Kabat equivalent>> refers to the EU numbering of the residues of human IgG1, IgG2, IgG3 or IgG4 antibodies. This is can be found on the IMGT website (http://www.imgt.org/IMGTScientificChart/Numbering/Hu_IGHGnber.html).

By <<polypeptide>> or <<protein>> is meant a sequence comprising at least 100 covalently bonded amino acids.

By <<amino acid>>, is meant one of the 20 natural amino acids or non-natural analogues.

The term <<position>> means a position in the sequence of a polypeptide. For the Fc region, the positions are numbered according to the EU index or Kabat equivalent.

The term <<antibody>> is used in its common meaning. It corresponds to a tetramer comprising at least one Fc region and two variable regions. Antibodies particularly comprise full-length immunoglobulins, monoclonal antibodies, multi-specific antibodies, chimeric antibodies, humanised antibodies and entirely human antibodies. The amino-terminal portion of each heavy chain comprises a variable region of about 100 to 110 amino acids and responsible for recognition of the antigen. In each variable region, three loops join together to form a binding site to the antigen. Each of the loops is called a complementarity determining region (CDR). The carboxy-terminal portion of each heavy chain defines a constant region chiefly responsible for the effector function.

IgGs have several sub-classes, in particular IgG1, IgG2, IgG3 and IgG4. The IgM sub-classes are particularly IgM1 and IgM2. Therefore, by <<isotype>> is meant one of the immunoglobulin sub-classes defined by the chemical and antigenic characteristics of their constant regions. The known isotypes of human immunoglobulins are IgG1, IgG2, IgG3, IgG4, IgA1, IgA2, IgM1, IgM2, IgD and IgE.

Full-length IgGs are tetramers and are composed of two identical pairs of two immunoglobulin chains, each pair having a light chain and a heavy chain, each light chain comprising the VL and CL domains, and each heavy chain comprising the domains VH, Cγ1 (also called CH1), Cγ2 (also called CH2) and Cγ3 (also called CH3). For a human IgG1, <<CH1>> refers to positions 118 to 215, <<CH2>> refers to positions 231 to 340 and <<CH3>> refers to positions 341 to 447 in the EU index or Kabat equivalent. The heavy chain of IgGs also comprises an N-terminal flexible hinge region which refers to positions 216 to 230 for IgG1. The lower hinge region refers to positions 226 to 230 in the EU Index or Kabat equivalent.

By "variable region" is meant the region of an immunoglobulin which comprises one or Ig domains substantially encoded by any of the genes Vκ, Vλ and/or VH which make up the kappa, lambda and heavy immunoglobulin chains, respectively. The variable regions comprise the complementarity determining regions (CDRs) and framework regions (FRs). The term "Fc" or "Fc region" designates the constant region of an antibody with the exclusion of the first immunoglobulin constant region domain (CH1). Therefore, Fc refers to the two last domains (CH2 and CH3) of the IgGI constant region, and to the N-terminal flexible hinge of these domains. For a human IgG1, the Fc region corresponds to residue C226 as far as its carboxy-terminal end, i.e. the residues at positions 226 to 447, numbered as in the EU index or Kabat equivalent. The Fc region used may further comprise part of the upper hinge region located between positions 216 to 226 in the EU Index or Kabat equivalent; in this case, the Fc region used corresponds to the residues at positions 216 to 447, 217 to 447, 218 to 447, 219 to 447, 220 to 447, 221 to 447, 222 to 447, 223 to 447, 224 to 447 or 225 to 447, numbered as in the EU Index or Kabat equivalent. Preferably, in this case, the Fc region used corresponds to the residues at positions 216 to 447, as numbered in the EU Index or Kabat equivalent.

Preferably, the Fc region used is selected from among the sequences SEQ ID NO: 1 to 10.

By <<parent polypeptide>> is meant a reference polypeptide. Said parent polypeptide may be of natural or synthetic origin. Within the context of the present invention, the parent polypeptide comprises an Fc region called <<parent Fc region>>. This Fc region can be selected from among the group of wild-type group Fc regions, the fragments or mutants thereof. Preferably, the parent polypeptide comprises a human Fc region, preferably an Fc region of a human IgG1. The parent polypeptide may comprise pre-existing modifications of amino acids in the Fc region (e.g. an Fc mutant) compared with wild-type Fc regions. Advantageously, the parent polypeptide parent is an isolated Fc region (i.e. an Fc fragment as such), a sequence derived from an isolated Fc region, an antibody, a fusion protein comprising an Fc region, or an Fc conjugate, this list being nonlimiting. By <<sequence derived from an isolated Fc region>> is meant a sequence comprising at least two isolated Fc regions that are linked together such as an scFc (single chain Fc) or multimer Fc. By <<fusion protein comprising an Fc region>> is meant a polypeptide sequence fused to an Fc region, said polypeptide sequence preferably being selected from among the variable regions of any antibody, the binding sequences of a receptor to its ligand, adhesion molecules, ligands, enzymes, cytokines and chemokines. By <<Fc conjugate>> is meant a compound that is the result of the chemical coupling of an Fc region with a conjugation partner. The conjugation partner may be proteinic or non-proteinic. The coupling reaction generally uses functional groups on the Fc region and the conjugation partner. Various binding groups are known in the prior art as being appropriate for synthesis of a conjugate: for example, homo- or heterobifunctional binding groups are well known (see, catalogue of the Pierce Chemical Company, 2005-2006, technical section on cross-linking agents, pages 321-350). Among suitable conjugation partners, mention can be made of therapeutic proteins, labels, cytotoxic agents such as chemotherapeutic agents, toxins and the active fragments thereof. Suitable toxins and their fragments notably include the diphtheria toxin, exotoxin A, ricin, abrin, saporin, gelonin, calicheamicin, auristatins E and F, and mertansine.

Advantageously, the parent polypeptide—and hence the polypeptide of the invention—consists of an Fc region.

Advantageously, the parent polypeptide—and hence the polypeptide of the invention—is an antibody.

Finally, preferably, the parent polypeptide—and hence the polypeptide of the invention—is a polypeptide produced in the milk of transgenic animals.

By <<mutation>> is meant a change of at least one amino acid in the sequence of a polypeptide, in particular a change of at least one amino acid in the Fc region of the parent polypeptide. The mutated polypeptide obtained is a variant polypeptide; it is a polypeptide of the invention. Said polypeptide comprises a mutated Fc region in comparison with the parent polypeptide. Preferably, the mutation is a substitution, insertion or deletion of at least one amino acid. By <<substitution>> is meant the replacement of one amino acid at a particular position in a parent polypeptide sequence by another amino acid. For example, substitution N434S refers to a variant polypeptide, here a variant in which asparagine at position 434 is replaced by serine. By "insertion of amino acid" or "insertion" is meant the addition of an amino acid at a particular position in a parent polypeptide sequence. For example, insertion G>235-236 designates an insertion of glycine between positions 235 and 236. By <<deletion of amino acids>> or <<deletion>> is meant the deletion of an amino acid at a particular position of a parent polypeptide sequence. For example, E294del designates the deletion of glutamic acid at position 294. Preferably, the following designation is used for mutation: <<434S>> or <<N434S>>, and indicates that the parent polypeptide comprises asparagine at position 434 replaced by serine in the variant. If there are a combination of substitutions, the preferred format is the following: <<259I/315D/434Y>> or <<V259I/N315D/N434Y>>. This indicates that there are three substitutions in the variant, at positions 259, 315 and 434, and that the amino acid at position 259 of the parent polypeptide i.e. valine is replaced by isoleucine, that the amino acid at position 315 of the parent polypeptide i.e. asparagine is replaced by aspartic acid and that the amino acid at position 434 of the parent polypeptide i.e. asparagine is replaced by tyrosine.

The polypeptide of the invention has functional activity, mediated by the Fc region, that is modified in comparison with that of the parent polypeptide.

By "functional activity mediated by the Fc region" is particularly meant the effector functions. The functional activity mediated by the Fc region therefore particularly comprises Antibody-Dependent Cell-mediated Cytotoxicity (ADCC), Complement Dependent Cytotoxicity (CDC), Antibody-Dependent Cell Phagocytosis (ADCP), endocytosis activity, cytokine secretion, or a combination of at least two of these activities. Preferably, the functional activity mediated by the Fc region under consideration in the invention is selected from among ADCC, CDC and the combination thereof. This functional activity can be evaluated using methods well known in the prior art such as those described in the examples (see in particular items 4.4 and 4.5 of the examples). The functional activity mediated by the Fc region of the polypeptide of the invention is increased or reduced compared with that of the parent polypeptide.

According to a first variant, the polypeptide of the invention has functional activity mediated by the Fc region that is increased in comparison to that of the parent polypeptide. Preferably, the polypeptide of the invention has functional activity mediated by the Fc region that is increased in relation to the parent polypeptide by a ratio of at least 2, preferably higher than 5, preferably higher than 10, preferably higher than 15, preferably higher than 20, preferably higher than 25 and preferably higher than 30.

According to a second variant, the polypeptide of the invention has functional activity mediated by the Fc region that is reduced compared with that of the parent polypeptide. Preferably, the polypeptide of the invention has functional activity mediated by the Fc region that is reduced in relation to that of the parent polypeptide by a ratio of at least 2, preferably higher than 5, preferably higher than 10, preferably higher than 15, preferably higher than 20, preferably higher than 25 and preferably higher than 30.

Preferably, the mutated Fc region of the polypeptide of the invention has modified affinity for at least one of the receptors (FcRs) of the Fc region, selected from among the C1q complement, FcgRIIIa (CD16a), FcgRIIa (CD32a) and FcgRIIb (CD32b). The C1q complement is involved in CDC activity. The FcgRIIIa receptor (CD16a) is involved in ADCC; it exhibits V/F polymorphism at position 158. The FcgRIIa receptor (CD32a) is involved in platelet activation and phagocytosis; it exhibits H/R polymorphism at position 131. Finally, the FcgRIIb receptor (CD32b) is involved in inhibition of cell activity. Preferably, said mutated Fc region has increased affinity for at least one of the FcRs. Preferably, the affinity is increased compared with that of the parent Fc by a ratio of at least 2, preferably higher than 5, preferably higher than 10, preferably higher than 15, preferably higher than 20, preferably higher than 25 and preferably higher than 30. In other words, the affinity of the mutated Fc region for an FcR is higher than that of the parent polypeptide. Alternatively, said mutated Fc region has reduced affinity for at least one of the FcRs. Preferably affinity is reduced in relation to that of the parent Fc by a ratio of at least 2, preferably higher than 5, preferably higher than 10, preferably higher than 15, preferably higher than 20, preferably higher than 25 and preferably higher than 30. In other words, the affinity of the mutated Fc region for an FcR is lower than that of the parent polypeptide.

The FcR affinity of a polypeptide comprising an Fc region can be evaluated with methods well known in the prior art. For example, persons skilled in the art can determine affinity (Kd) using surface plasma resonance (SPR). Alternatively, skilled persons can perform a suitable ELISA assay. Suitable ELISA assay allows a comparison between the binding forces of the parent Fc and mutated Fc. The detected signals specific to the mutated Fc and parent Fc are compared. Binding affinity can be determined indifferently whether evaluating whole polypeptides or isolated Fc regions thereof.

Preferably, the mutated Fc region of the invention comprises 1 to 20 mutations compared with the parent polypeptide, preferably 2 to 20 mutations. By <<1 to 20 modifications of amino acids>> this encompasses 1, 2, 3, 4, 5, 6, 7, 8, 9, 10, 11, 12, 13, 14, 15, 16, 17, 18, 19 and 20 mutations of amino acids. Preferably, it comprises 1 to 15 mutations, preferably 2 to 15 mutations, preferably 1 to 10 mutations in relation to the parent polypeptide, preferably 2 to 10 mutations.

Preferably, the mutated Fc region of the polypeptide of the invention comprises at least one combination of 2 mutations, said combination being selected from among:
 (i) one mutation selected from among 378V, 396L and 397M;
 (ii) at least one mutation selected from among 231V, 248E, 286I, 286Y, 290E, 298N, 308A, 315D, 316D, 326E, 333G, 334N, 334R, 336T, 352S, 361H, 366A, 378T, 396L, 397M, 412M, 421T, 423Y and 447N,
the numbering being that of the EU Index or Kabat equivalent, and provided that mutation (i) does not take place on the same amino acid as mutation (ii).

Preferably, the mutated Fc region of the polypeptide of the invention comprises at least one combination of 2 mutations, said combination being selected from among:
 (i) one mutation selected from among 378V, 396L et 397M;
 (ii) at least one mutation selected from among 248E, 316D, 326E, 333G, 378T, 396L and 421T,
the numbering being that of the EU Index or Kabat equivalent, and provided that mutation (i) does not take place on the same amino acid as mutation (ii).

Preferably, the polypeptide of the invention comprises a mutated Fc region having increased ADCC and CDC functional activities compared with those of the parent polypeptide, characterized in that said Fc region comprises at least one combination of 2 mutations, said combination being selected from among:
 (i) one mutation selected from among 378V, 396L and 397M;
 (ii) at least one mutation selected from among 248E, 316D, 326E, 333G, 378T, 396L and 421T, the numbering being that of the EU Index or Kabat equivalent, and provided that mutation (i) does not take place on the same amino acid as mutation (ii).

Preferably, the mutated Fc region of the polypeptide of the invention comprises at least one combination of 2 mutations, said combination being selected from among:
(i) mutation 378V;
(ii) at least one mutation selected from among 298N and 336T, the numbering being that of the EU Index or Kabat equivalent, and provided that mutation (i) does not take place on the same amino acid as mutation (ii).

Preferably, the mutated Fc region of the polypeptide of the invention comprises at least one combination of 2 mutations, said combination being selected from among:
(i) one mutation selected from among 378V, 396L and 397M;
(ii) at least one mutation elected from among 231V, 286I, 286Y, 290E, 315D, 334N, 352S, 361H, 366A, 378T, 397M, 412M, 421T and 423Y, the numbering being that of the EU Index or Kabat equivalent, and provided that mutation (i) does not take place on the same amino acid as mutation (ii).

Preferably, the polypeptide of the invention comprises a mutated Fc region having increased ADCC functional activity compared with that of the parent polypeptide, characterized in that said Fc region comprises at least one combination of 2 mutations, said combination being selected from among:
(i) one mutation selected from among 378V, 396L and 397M;
(ii) at least one mutation selected from among 231V, 286I, 286Y, 298N, 290E, 315D, 334N, 336T, 352S, 361H, 366A, 378T, 397M, 412M, 421T and 423Y, the numbering being that of the EU Index or Kabat equivalent, and provided that mutation (i) does not take place on the same amino acid as mutation (ii).

Preferably, the mutated Fc region of the polypeptide of the invention comprises at least one combination of 2 mutations, said combination being selected from among:
(i) mutation 378V;
(ii) at least one mutation selected from among 248E, 308A, 334R, 447N, the numbering being that of the EU Index or Kabat equivalent, and provided that mutation (i) does not take place on the same amino acid as mutation (ii).

Preferably, the polypeptide of the invention comprises a mutated Fc region having increased CDC functional activity compared with that of the parent polypeptide, characterized in that said Fc region comprises at least one combination of 2 mutations, said combination being selected from among:
(i) mutation 378V;
(ii) at least one mutation selected from among 248E, 308A, 334R, 447N, the numbering being that of the EU Index or Kabat equivalent, and provided that mutation (i) does not take place on the same amino acid as mutation (ii).

Preferably, the mutated Fc region of the polypeptide of the invention comprises a combination of mutations selected from among the combinations:
K320E/T394P/G402D
K290E/K320E/T350A/P396L
T359A/S383R/V397M Preferably, the mutated Fc region of the polypeptide of the invention has improved affinity for the C1q complement, and comprises at least one combination of 2 mutations, said combination comprising:

i) one mutation selected from among 378V, 378T, 396L, 421T, 334R and 326E; and
ii) at least one mutation selected from among 361H, 290E, 316D, 248E, 410R, 421T, 334R, 394P, 307P, 447N, 378V, 284L, 421T, 396L, 286I, 315D and 397M, the numbering being that of the EU Index or Kabat equivalent, and provided that mutation (i) does not take place on the same amino acid as mutation (ii).

Preferably, the mutated Fc region of the polypeptide of the invention has improved affinity for the FcgRIIIa receptor (CD16a), and comprises at least one combination of 2 mutations, said combination comprising:
i) one mutation selected from among 378V, 326E, 397M, 334N and 396L; and
ii) at least one mutation selected from among 316D, 397M, 334N, 248E, 231V, 246R, 336T, 421T, 361H, 366A, 439R, 290E, 394P, 307P, 378V, 378T, 286I, 286Y and 298N, the numbering being that of the EU Index or Kabat equivalent, and provided that mutation (i) does not take place on the same amino acid as mutation (ii).

Preferably, the mutated Fc region of the polypeptide of the invention has increased affinity for the FcgRIIa receptor (CD32a), and comprises at least one combination of 2 mutations, said combination comprising:
i) one mutation selected from among 378V, 326E, 397M, 307N, 394P, 326T, 396L and 334N; and
ii) at least one mutation selected from among: 316D, 334R, 334N, 323I, 231V, 246R, 336T, 378T, 286Y, 286I, 352S, 383R, 359A, 421T, 361H, 315D, 366A, 290E, 307P and 439R, the numbering being that of the EU Index or Kabat equivalent, and provided that mutation (i) does not take place on the same amino acid as mutation (ii).

Preferably, mutation (ii) is selected from among: 316D, 334R, 334N, 323I, 231V, 246R, 336T, 378T, 286Y, 286I, 352S, 383R, 359A, 421T, 361H, 366A, 290E, 307P and 439R.

Preferably, the mutated Fc region of the polypeptide of the invention has increased affinity for the FcgRIIb receptor (CD32b), and comprises at least one combination of 2 mutations, said combination comprising:
i) one mutation selected from among 326E, 326T, 378V, 397M, 352L, 394P, 396L and 421T; and
ii) at least one mutation selected from among 316D, 334R, 248E, 334N, 418P, 231V, 320E, 402D, 359A, 383R, 421T and 361H, the numbering being that of the EU Index or Kabat equivalent, and provided that mutation (i) does not take place on the same amino acid as mutation (ii).

Preferably, the mutated Fc region of the polypeptide of the invention has increased CDC activity, and comprises at least one combination of 2 mutations, said combination comprising:
i) one mutation selected from among 378V, 378T, 396L, 421T, 334R and 326E; and
ii) at least one mutation selected from among 361H, 290E, 316D, 248E, 410R, 421T, 334R, 394P, 307P, 447N, 378V, 284L, 421T, 396L, 286I, 315D and 397M, the numbering being that of the EU Index or Kabat equivalent, and provided that mutation (i) does not take place on the same amino acid as mutation (ii).

Preferably, the mutated Fc region of the polypeptide of the invention has increased ADCC activity, and comprises at least one combination of 2 mutations, said combination comprising:

i) one mutation selected from among 378V, 326E, 397M, 334N and 396L; and
ii) at least one mutation selected from among 316D, 397M, 334N, 248E, 231V, 246R, 336T, 421T, 361H, 366A, 439R, 290E, 394P, 307P, 378V, 378T, 286I, 286Y and 298N, the numbering being that of the EU Index or Kabat equivalent, and provided that mutation (i) does not take place on the same amino acid as mutation (ii).

Preferably, the mutated Fc region of the polypeptide of the invention comprises at least one combination of 3 mutations, said combination comprising:
(i) one mutation selected from among 326E, 326T, 352L, 378V, 378T, 396L, 397M, 421T, 334N, 334R, 307N and 394P; and
(ii) at least 2 mutations selected from among 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N, the numbering being that of the EU Index or Kabat equivalent, and provided that mutation (i) does not take place on the same amino acid as mutation (ii).

Preferably, the at least 2 mutations (ii) are selected from among 226Y, 227S, 230S, 231V, 234P, 243I, 243L, 246R, 246E, 247T, 248E, 253F, 254F, 255W, 259A, 261R, 262A, 263A, 266M, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378T, 379A, 380G, 383R, 385R, 389S, 389T, 392R, 393A, 393I, 394P, 396L, 397I, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P, and 447N.

More preferably, the mutated Fc region of the polypeptide of the invention comprises at least one combination of 4 mutations, said combination comprising at least one mutation (i) such as described above, and at least 3 mutations (ii) such as described above, the numbering being that of the EU Index or Kabat equivalent, and provided that mutation (i) does not take place on the same amino acid as mutation (ii).

More preferably, the mutated Fc region of the polypeptide of the invention comprises at least one combination of 5 mutations, said combination comprising at least one mutation (i) such as described above, and at least 4 mutations (ii) such as described above, the numbering being that of the EU Index or Kabat equivalent, and provided that mutation (i) does not take place on the same amino acid as mutation (ii).

A further subject of the present invention is a composition of polypeptides of the invention, said purified polypeptides on their Asn297 glycosylation site having N-glycans with a fucosylation rate lower than 65%, preferably lower than 50%, more preferably lower than 40%. Preferably said purified polypeptides, on their Asn297 glycosylation site, have a glycan structure of biantennary type with short chains, low sialylation, having non-intercalary terminal mannoses and/or non-intercalary terminal N-acetylglucosamines. More preferably, said purified polypeptides have a content higher than 60% for the G0+G1+G0F+G1F forms, the content being lower than 50% for the G0F+G1F forms. More preferably, said purified polypeptides have a content higher than 60% for the G0+G1+G0F+G1F forms, the fucose content being lower than 65%, More preferably, said purified polypeptides have a content lower than 40% for the G1F+G0F forms.

A further subject of the present invention is a pharmaceutical composition comprising (i) a polypeptide of the invention or a composition such as described in the preceding paragraph and (ii) at least one pharmaceutically acceptable excipient.

A further subject of the present invention is the polypeptide of the invention or the composition such as previously described for use as medicinal product.

As previously indicated, advantageously the parent polypeptide—and hence the polypeptide of the invention—is an antibody. In this case, the antibody can be directed against a tumour antigen, viral antigen, bacterial antigen, fungal antigen, a toxin, membrane-bound or circulating cytokine, and a membrane receptor.

When the antibody is directed against a tumour antigen, it is particularly suitable for use in the treatment of cancers. By <<cancer>> is meant any physiological condition characterized by abnormal cell proliferation. Examples of cancers notably include carcinoma, lymphoma, blastoma, sarcoma (including liposarcoma), neuroendocrine tumours, mesothelioma, meningioma, adenocarcinoma, melanoma, leukaemia and malignant lymphoid pathologies, this list being non-exhaustive.

When the antibody is directed against a viral antigen, it is particularly suitable for use in the treatment of viral infections. Viral infections in particular are infections due to HIV, a retrovirus, Coxsackie virus, smallpox virus, influenza virus, yellow fever virus, West Nile virus, to a cytomegalovirus, to a rotavirus or to the hepatitis B or C virus, this list being non-exhaustive.

When the antibody is directed against a toxin, it is particularly suitable for use in the treatment of bacterial infections e.g. infections with the tetanus toxin, diphtheria toxin, *Bacillus anthracis* toxins, or for the treatment of infections with botulin toxins, ricin toxins, shiga toxins, this list being non-exhaustive.

When the antibody is directed against a cytokine, it is particularly suitable for use in the treatment of inflammatory and/or autoimmune diseases. Inflammatory and/or autoimmune diseases notably include thrombotic thrombocytopenic purpura (TTP), graft or transplant rejection, graft-versus-host-disease, rheumatoid polyarthritis, systemic lupus erythematosus (SLE), different types of sclerosis, primary Sjögren's syndrome (or Gougerot-Sjögren syndrome), autoimmune polyneuropathies such as multiple sclerosis, type I diabetes, autoimmune hepatitis, ankylosing spondylitis, Reiter's syndrome, gouty arthritis, celiac disease, Crohn's disease, chronic Hashimoto thyroiditis (hypothyroidism), Addison's disease, autoimmune hepatitis, Basedow's disease (hyperthyroidism), ulcerative colitis, vasculitis such as ANCA-associated systemic vasculitis (AntiNeutrophil Cytoplasmic Autoantibodies), autoimmune cytopenia and other haematological complications in adults and children such as autoimmune acute or chronic thrombopenia, autoimmune haemolytic anaemia, haemolytic disease of the newborn (HDN), cold agglutinin disease, autoimmune acquired haemophilia; Goodpasture syndrome, membranous nephropathy, autoimmune skin blistering disorders, refractory myasthenia, mixed cryoglobulinemia, psoriasis, juvenile chronic arthritis, inflammatory myositis, dermatomyositis and systemic autoimmune disorders in children including paediatric antiphospholipid syndrome, connective tissue disease, autoimmune lung inflammation, Guillain-Barre syndrome, chronic inflammatory demyelinating polyneuropathy (CIDP), autoimmune thyroiditis, mellitis, myasthenia gravis, autoimmune ocular inflammatory disease, neuromyelitis optica (Devic's disease), scleroderma, pemphigus, diabetes through insulin resistance, polymyositis, Biermer's anaemia, glomerulonephritis, Wegener's disease, Horton disease, polyarteritis *nodosa* (PAN) and Churg-Strauss syndrome, Still's disease, atrophic polychondritis, Behcet's disease, monoclonal gammopathy, Wegener granulomatosis, lupus, haemorrhagic rectocolitis, psoriatic arthritis, sarcoidosis collagenous colitis, dermatitis herpetiformis, familial Mediterranean fever, la glomerulonephritis with IgA deposits, Lambert-Eaton myasthenic syndrome, sympathetic ophthalmia, Fiessinger-Leroy-Reiter syndrome and uveo-meningo-encephalitic syndrome.

Other inflammatory diseases are also included, such as for example the acute respiratory distress syndrome (ARDS), acute septic arthritis, adjuvant arthritis, allergic encephalomyelitis, allergic rhinitis, allergic vasculitis, allergy, asthma, atherosclerosis, chronic inflammation due to chronic bacterial or viral infections, chronic obstructive pulmonary disease (COPD), coronary disease, encephalitis, intestinal inflammatory diseases, inflammatory osteolysis, inflammation associated with acute and delayed hypersensitivity reactions, inflammation associated with tumours, peripheral nerve lesion or demyelinising diseases, inflammation associated with tissue trauma such as burns and ischaemia, inflammation due to meningitis, multiple organ dysfunction syndrome (MODS), pulmonary fibrosis, septicaemia and septic shock, Stevens-Johnson syndrome, undifferentiated arthritis, and undifferentiated spondyloarthropathies.

In one particular embodiment of the invention, the autoimmune disease is idiopathic thrombocytopenic purpura (ITP) and chronic inflammatory demyelinating polyneuropathy (CIDP).

A further subject of the invention is a method to produce a polypeptide comprising an Fc region and having functional activity, mediated by the Fc region, that is modified in comparison with that of a parent polypeptide, said method comprising a step to introduce at least one mutation in said Fc region, selected from among:
G316D, K326E, N315D, N361H, P396L, T350A, V284L, V323I, P352S, A378V, Y436H, V266M, N421T, G385R, K326T, H435R, K447N, N434K, K334N, V397M, E283G, A378T, F423L, A431V, F423S, N325S, P343S, K290E, S375R, F405V, K322E, K340E, N389S, F243I, T307P, N389T, S442F, K248E, Y349H, N286I, T359A, S383R, K334R, T394P, V259A, T393A, P352L, Q418P, V302A, L398P, F423P, S442P, V363I, S383N, S254F, K320E, G402D, I253F, V284A, A431T, N315H, Y319H, C226Y, F405L, T393I, N434S, R255W, A287T, N286Y, A231V, K274R, V308G, K414R, M428T, E345G, F243L, P247T, Q362R, S440N, Y278H, D312G, V262A, V305A, K246R, V308I, E380G, N276S, K439Q, S267G, F423Y, A231T, K320R, L410R, K320M, V412M, T307N, T366A, P230S, Y349S, A339T, K246E, K274E, A231P, I336T, S298N, L234P, S267N, V263A, E333G, V308A, K439R, K392R, S440G, V397I, I336V, Y373D, K288E, L309P, P227S, V379A, K288R, K320T, V282A, I377T, N421S and C261R, the numbering being that of the EU Index or Kabat equivalent.

Preferably, the subject of the present invention is a method to produce a polypeptide comprising an Fc region and having functional activity, mediated by the Fc region, that is modified in comparison with that of a parent polypeptide, said method comprising a step to introduce at least one combination of 2 mutations, said combination being selected from among:

(i) one mutation selected from among 326E, 326T, 352L, 378V, 378T, 396L, 397M, 421T, 334N, 334R, 307N and 394P; and (ii) at least one mutation selected from among 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P, and 447N,
the numbering being that of the EU Index or Kabat equivalent, provided that mutation (i) does not take place on the same amino acid as mutation (ii).

Preferably, mutation (ii) is selected from among 226Y, 227S, 230S, 231V, 234P, 243I, 243L, 246R, 246E, 247T, 248E, 253F, 254F, 255W, 259A, 261R, 262A, 263A, 266M, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378V, 379A, 380G, 383R, 385R, 389S, 389T, 392R, 393A, 393I, 394P, 396L, 397I, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P, and 447N.

A further subject of the present invention is a method to increase the binding of a polypeptide comprising an Fc region with at least one of the receptors (FcR) of the Fc region selected from among the receptors C1q, FcgRIIIa (CD16a), FcgRIIa (CD32a) and FcgRIIb (CD32b), said method comprising a step to introduce at least one mutation in said Fc region, selected from among:
G316D, K326E, N315D, N361H, P396L, T350A, V284L, V323I, P352S, A378V, Y436H, V266M, N421T, G385R, K326T, H435R, K447N, N434K, K334N, V397M, E283G, A378T, F423L, A431V, F423S, N325S, P343S, K290E, S375R, F405V, K322E, K340E, N389S, F243I, T307P, N389T, S442F, K248E, Y349H, N286I, T359A, S383R, K334R, T394P, V259A, T393A, P352L, Q418P, V302A, L398P, F423P, S442P, V363I, S383N, S254F, K320E, G402D, I253F, V284A, A431T, N315H, Y319H, C226Y, F405L, T393I, N434S, R255W, A287T, N286Y, A231V, K274R, V308G, K414R, M428T, E345G, F243L, P247T, Q362R, S440N, Y278H, D312G, V262A, V305A, K246R, V308I, E380G, N276S, K439Q, S267G, F423Y, A231T, K320R, L410R, K320M, V412M, T307N, T366A, P230S, Y349S, A339T, K246E, K274E, A231P, I336T, S298N, L234P, S267N, V263A, E333G, V308A, K439R, K392R, S440G, V397I, I336V, Y373D, K288E, L309P, P227S, V379A, K288R, K320T, V282A, I377T, N421S and C261R, the numbering being that of the EU Index or Kabat equivalent.

Preferably, the subject of the present invention is a method to increase the binding of a polypeptide comprising an Fc region to at least one of the receptors (FcR) of the Fc region, selected from among the receptors C1q, FcgRIIIa (CD16a), FcgRIIa (CD32a) and FcgRIIb (CD32b), said method comprising a step to introduce at least one combination of 2 mutations, said combination being selected from among:
  (i) one mutation selected from among 326E, 326T, 352L, 378V, 378T, 396L, 397M, 421T, 334N, 334R, 307N and 394P; and
  (ii) at least one mutation selected from among 226Y, 227S, 230S, 231V, 234P, 243I, 243L, 246R, 246E, 247T, 248E, 253F, 254F, 255W, 259A, 261R, 262A, 263A, 266M, 267N, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 315D, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378V, 378T, 379A, 380G, 383R, 385R, 389S, 389T, 392R, 393A, 393I, 394P, 396L, 397I, 397M, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N,
the numbering being that of the EU Index or Kabat equivalent, and provided that mutation (i) does not take place on the same amino acid as mutation (ii).

Preferably, mutation (ii) is selected from among 226Y, 227S, 230S, 231V, 234P, 243I, 243L, 246R, 246E, 247T, 248E, 253F, 254F, 255W, 259A, 261R, 262A, 263A, 266M, 267G, 274E, 274R, 276S, 278H, 282A, 283G, 284L, 286I, 286Y, 287T, 288E, 288R, 290E, 298N, 302A, 305A, 307P, 308A, 308I, 308G, 309P, 312G, 316D, 319H, 320T, 320R, 320M, 322E, 323I, 325S, 333G, 334N, 334R, 336T, 339T, 340E, 343S, 345G, 349S, 349H, 350A 352S, 359A, 361H, 362R, 363I, 366A, 373D, 375R, 377T, 378T, 379A, 380G, 383R, 385R, 389S, 389T, 392R, 393A, 393I, 394P, 396L, 397I, 398P, 405V, 405L, 410R, 412M, 414R, 421T, 421S, 423L, 423Y, 423S, 423P, 428T, 431V, 431T, 434K, 434S, 435R, 436H, 439R, 440G, 440N, 442F, 442P and 447N.

The sequences described in the present application can be summarised as follows:

| SEQ ID NO: | Protein |
|---|---|
| 1 | Fc region of human IgGI, G1m1,17 (residues 226-447 in EU Index or Kabat equivalent) without N-terminal upper hinge region. |
| 2 | Fc region of human IgG2 without N-terminal upper hinge region. |
| 3 | Fc region of human IgG3 without N-terminal upper hinge region. |
| 4 | Fc region of human IgG4 without N-terminal upper hinge region. |
| 5 | Fc region of human IgG1, G1m3, without N-terminal upper hinge region. |
| 6 | Fc region of human IgG1, G1m1,17, with N-terminal upper hinge region (residues 216-447 in EU Index or Kabat equivalent). |
| 7 | Fc region of human IgG2 with N-terminal upper hinge region. |
| 8 | Fc region of human IgG3 with N-terminal upper hinge region. |
| 9 | Fc region of human IgG4 with N-terminal upper hinge region. |
| 10 | Fc region of human IgG1, G1m3, with N-terminal upper hinge region. |
| 11 and 12 | Primers MG_619 and MG_621 |

The present invention will be better understood on reading the following examples.

EXAMPLES

Example 1: Identification of Polypeptides with Mutated Fc Region of the Invention and Characterization of Said Polypeptides I. Material and Methods 1. Construction of Banks of the Human Fc Region The human Fc gene encoding the amino acids 226-447 (EU Index or Kabat equivalent) i.e. a polypeptide comprising an Fc region, derived from a heavy chain of human IgG1 and having the allotype G1 m1.17 (SEQ ID NO: 1), (Poul M A et al, Eur J. Immunol 25 (7): 2005-2009, 1995) was cloned in the phagemid vector pMG58 (pMG58_Fc226) as BamHI/EcoRI fragment following standard PCR protocols. Several fully randomized banks were generated applying the MUTAGEN™ method (WO02/038756) which uses low-fidelity human DNA-polymerases (mutases) to introduce random mutations homogeneously in the entire target sequence. Three different mutases (pol β, pol η and pol ι) were used under different conditions to create complementary mutation profiles. These human polymerases were produced and purified as previously described (Mondon et al. J. Biotechnol 21: 76-82 (2007), Emond et al. Protein Eng Des Sel 21:267-274, (2008)).

1.1. Mutagenesis with the MUTAGEN™ Method

The MUTAGEN™ method was described in application WO02/038756.

In brief, the human Fc gene (Fc gene) was replicated with mutases using the 5' primer MG_619: 5'-AGTACTGACTC-TACCTAGGATCCTGCCCACCGTGC-3' (SEQ ID NO: 11) and the 3' primer MG_621: 5'-ACTGCTC-GATGTCCGTACTATGCGGCCGCGAATTC-3' (SEQ ID NO: 12). A mixture containing 0.6 µg of the pMG58_Fc226 plasmid as model (wild-type Fc region or selected variants), the primers MG_619 and MG_621 (250 nM each) and suitable replication buffer (see details below) was treated for 5 min at 95° C. and immediately cooled to 4° C. to denature the DNA strands. For pol R, the replication buffer was 50 mM Tris HCl pH 8.8, 10 mM MgCl2, 10 mM KCl, 1 mM DTT and 1% (v/v) glycerol. The replication buffer for pol η (or pol η and pol ι) was 25 mM Tris HCl pH 7.2, 5 mM MgCl2, 10 mM KCl, 1 mM DTT and 2.5% (v/v) glycerol. After the denaturing step, mutagenic replications were obtained by adding 50 µM ATP/dCTP, 100 µM dTTP/dGTP and 1 µg of pol β or 100 µM of dNTP and 1 µg of pol η (or pol η and pol ι, 1 µg of each mutase). The replication reaction was conducted at 37° C. for two hours. The replication products were subsequently concentrated and desalted on Microcon columns (Millipore).

1.2. Selective Amplification and Cloning of the Mutated Fragments

The previously obtained replication products were amplified by selective PCR with tail primers. The primers (MG_619 MG_621) were designed with a tail that was non-complementary to the model allowing specific amplification of the DNA fragments synthesized by the mutases. One fraction of the replication products was added to a mixture containing the PCR buffer (20 mM Tris-HCl pH 8.4, 50 mM KCl), 1.5 mM MgCl2, 10 pmol of the 5' and 3' primers, 200 µM of dNTPs and 1.25 U of Platinum Taq DNA polymerase (Invitrogen). The PCR cycles were: first cycle 2 min. at 94° C., 10 sec. at 64° C., 30 sec. at 75° C., 1 min. at 94° C., followed by 30 selective cycles: 20 sec. at 94° C. and 30 sec. at 75° C.

The amplified replication products were purified on 1% (w/v) of agarose gels digested with BamHI and EcoRI and cloned in the pMG58 vector. The ligation mixtures were transformed in *E. Coli* XL1-Blue electrocompetent cells and spread over a solid 2YT medium (16 g/l peptone, 10 g/l yeast extract, 5 g/l NaCl, 15 g/l agar) to which were added 100 µg/ml of ampicillin and 1% (w/v) glucose. After growth, the number of colonies was determined to estimate the size of the banks and at least 48 clones per bank were subjected to PCR and fast DNA sequencing. The cells were re-suspended in the 2YT medium with 15% glycerol, frozen and stored at −80° C.

1.3. Construction of the Mut3 Bank

A first bank was obtained using pol β on the wild-type Fc gene and contained $3.2\times10^6$ clones (called Mut1.1). The DNA of this first bank was used to generate the second and third banks, respectively using pol β ($3.8\times10^6$ clones, Mut1.2) and pol η and i ($3.0\times10^6$ clones, Mut1.3). This strategy with two accumulated replication steps allowed an increase in the mutation rate. The fourth bank was obtained with pol η alone on the wild-type Fc gene ($1.0\times10^6$ clones, Mut1.4). Finally, these four banks were proportionately mixed to obtain the final bank called Mut1, representing $1.1\times10^7$ different clones.

Two different banks were then constructed using a DNA pool of single and double mutants isolated on the FcRn receptor. A first bank was obtained using pol β ($1.9\times10^7$ clones, Mut2.1) and a second bank with pol η ($1\times10^6$ clones, Mut2.2). Finally, these two banks were proportionately mixed to obtain the final bank called Mut2, i.e. $2\times10^7$ different clones.

A new bank was obtained using pol β on the wild-type Fc gene, with a diversity of $4.7\times10^7$ clones.

Finally, the banks Mut1, Mut2 and the new bank were proportionately mixed to obtain the final bank called Mut3, i.e. $7.8\times10^7$ different clones.

The Mut3 bank finally contained $3\times10^7$ mutated clones in phase with a mean of 2.2 mutated amino acids per Fc.

1.4. Construction of the Mut4sel Bank

A bank of Fc variants was constructed from 36 clones having improved binding with C1q and/or CD16aV, selected from the Mut3 bank Mut3 (1.6 mutated amino acids per Fc on average). The Mut4 bank was obtained using an equimolar mixture of pol β and pol polymerases (in the replication buffer of pol β). The Mut4 bank has a diversity of $1.3\times10^7$ clones, with 77% of clones in phase and on average 2.6 mutated amino acids per Fc. This bank was cloned in the pMG93 vector, a selection vector developed for Fc which allows selection of the coding sequences (ORFs) on an ampicillin medium through fusion with the gene of □-lactamase. This construction was transformed in the non-suppressive bacteria HB2151, which allowed removal of the TAGs codons that are known to be stop codons in this strain. The clones of this bank were spread plated in low density in dishes of agar medium containing small amounts of ampicillin, to carry out selection of the ORFs, the viable clones then being recovered and frozen. Spread plating in 500 Petri dishes (120×120) allowed covering of the entire bank Mut4. The bank thus selected was denoted Mut4sel and contained 92% clones in phase, i.e. $1\times10^7$ mutated clones in phase, with an average of 2.5 mutated amino acids per Fc. The Mut4sel bank was then sub-cloned in the phagemid pMG58, in XL1-Blue bacteria, to allow selection by <<phage display>> on the targets.

1.5. Construction of the Mut5 Bank

A bank of Fc variants was constructed from 42 clones having improved binding with C1q and/or one of the FcgR receptors, selected from the Mut4sel bank (2.4 mutated amino acids per Fc on average). The Mut5 bank was obtained using the polymerase pol β alone so as to obtain a low mutation rate. Finally, the Mut5 bank obtained contained $1.2\times10^7$ clones with 95% clones in phase and on average 3.1 mutated amino acids per Fc. The good quality of this bank did not require the selection of ORFs as was required for the Mut4 bank.

2. Phage Display Expression of the Fc Banks and Selection of the Improved Variants At the selection steps, the banks Mut3, Mut4sel and Mut5 were expressed on the surface of the M13 bacteriophage following standard procedures (Smith G P, Science 228: 1315 (1985)). *E. coli* XL1-Blue bacteria, containing the bank to be expressed cloned in the pMG58 vector, were cultured in 60 ml of 2YT medium to which were added 100 µg/ml ampicillin, 15 µg/ml tetracycline and 1% (w/v) glucose at 30° C. The cells were then infected with the auxiliary phage M13 (M13K07, Biolabs, bacteria/phage ratio=1:3) at 37° C. for 20 min and the production of Fc-phage was continued overnight at 26° C., at 230 rpm 2YT/ampicillin/glucose with 0.5 mM IPTG and 50 µg kanamycin/ml. The following day, the phages were precipitated with PEG6000 following standard procedures, re-suspended in 1 ml of PBS buffer at pH 7.4 and titrated by infecting XL1-Blue cells.

2.1 Recombinant Proteins Used:

The C1q complement is commercially available (Calbiochem).

CD16a is an activator receptor having V/F polymorphism at position 158, on the binding side to Fc. Affinity is improved for CD16aV.

CD16aV is commercially available (R&D system).

CD16aF was produced by PX'Therapeutics.

CD32a is an activator receptor having H/R polymorphism at position 131, on the binding site to Fc. Affinity is improved for CD32aH.

CD32aR is commercially available (R&D system).

CD32aH was produced by PX'Therapeutics. CD32b is an inhibitor receptor having lesser affinity for IgG1s than CD32aR. It is commercially available (R&D system).

2.2. Solid Phase Selections:

For solid phase selections, the Fc-phages diluted in PBS/ 5% skim milk/0.1% Tween 20 were incubated in 8 wells of Maxisorp plates ($1-4\times10^{11}$ phages/well in final 100 µl) previously coated with 500 ng/well of CD16aV, biotinylated CD16aV, biotinylated CD16aF, biotinylated C1q, biotinylated CD32aR or biotinylated CD32b and blocked with 5% skim milk in PBS. After incubation for 2 hours at 37° C., the wells were washed 8 times with PBS/0.1% Tween 20, and 2 times with PBS. For selections on CD32aR and CD32b, counter-selection rounds were also carried out: before the binding step on the target immobilised on a Maxisorp plate, the Fc-phages were pre-incubated in similar manner on 8 wells with the competitive receptor. Only the non-bonded Fc-phages on the first target were then transferred into wells containing the second target as previously described. The selected phages were eluted by infection with XL1-Blue bacteria in exponential growth phase (2×150 µl/well, 20 min. at 37° C. without agitation). The infected bacteria were spread plated on a solid 2YT/ampicillin/glucose medium. The following day, the cells were re-suspended in 2YT medium with 15% glycerol, frozen and stored at −80° C. until the following selection round.

2.3. Liquid Phase Selections:

For liquid phase selections, $4 \times 10^{11}$ phages were first incubated with biotinylated CD16aV (250 nM), biotinylated CD16aF (1000 nM), or with biotinylated C1q (250 nM) for 1 hour at ambient temperature under light agitation. Magnetic beads coated with streptavidin (Dynal) previously blocked with 5% skim milk in PBS were then added to the phages for 30 minutes at ambient temperature. The phage-bead complexes were washed 10 times with PBS/0.1% Tween 20 using a magnet. The phage-bead complexes were used to infect 5 ml of XL1-Blue bacteria in exponential growth that were spread plated on a solid 2YT/ampicillin/glucose medium. The following day, the cells were re-suspended in 2YT medium with 15% glycerol, frozen and stored at −80° C. until the following selection round.

2.4. Selections from Banks:

Mut3 Bank:

For liquid phase selections, 6 rounds were performed on 3 biotinylated targets: CD16aV, CD16aF and C1q (clones denoted DL6A, DL6B and QL6A). For the solid phase selection rounds, 6 rounds were performed on 3 targets: CD16aV, biotinylated CD16aV and biotinylated C1q (clones denoted DS6A, DS6B and QS6A).

Mut4sel Bank:

The selection rounds were solely conducted in solid phase: 3 selection rounds on biotinylated CD16aV, 3 rounds on biotinylated C1q, 3 rounds on biotinylated CD32aR (+/−depletion on CD32b for the $3^{rd}$ round) and 3 rounds on biotinylated CD32b (+/−depletion on CD32aR for the $3^{rd}$ round), (clones denoted A3A, G3A, J3A/B and K3A/B).

Mut5 Bank:

The selection rounds were conducted as previously: 3 selection rounds on biotinylated CD16aF, 3 rounds on biotinylated C1q, 3 rounds on biotinylated CD32aR, 3 rounds on biotinylated CD32b, 2 rounds on biotinylated CD32aR and 2 rounds with depletion on biotinylated CD32b, and 2 rounds on biotinylated CD32b and 2 depletion rounds on biotinylated CD32aR (clones denoted N3A, O3A, P3A, Q3A, P4B and Q4B).

Selection was then performed as previously described.

2.5. Pool Cloning in the pMGM05 Vector:

The clones selected after the selection rounds were directly transferred in a mixture (about $10^4$ clones per condition) into the eukaryote vector pMGM05-CD20 (pCEP4 InvitroGen), which contains the same cloning sites as the pMG58 phagemid for the Fc fragment (BamHI and NotI) and the VH variable chain of the anti-CD20 antibody. This construction leads to mutation of two amino acids in Fc (aa224 and 225, HT changed to GS) and addition of the EFAAA sequence at the C-terminal of Fc, but allows rapid testing of a very large number of clones. It was initially verified that these mutations do not modify the binding of IgG-WT to the different receptors. Thereafter, the positive controls were cloned in this system for validation thereof:

IgG1-S239D, I332E, derived from the anti-CD19 XmAb5574 antibody by Xencor (C1): positive control for CD16a;

IgG1-G236A, derived from Xencor (C4): positive control for CD32aH/R;

IgG1-K326W, E333S, derived from Abgenix/Genentech (C3): positive control for C1q; and IgG1-S267E, L328F, derived from the anti-CD19 XmAb5574 antibody by Xencor (C5): positive control for CD32b.

The DNA of about one hundred clones, isolated by selection rounds, were sequenced by PCR on colonies. After bioinformatic analyses, the clones comprising new mutations were frozen at −80° C. in XL1-Blue bacteria and the sequences included in our database. As a result, 158 clones were isolated from the Mut3 bank, 371 clones from the Mut4sel bank and 171 clones from the Mut5 bank.

2.6. Production of Variants in HEK293 Cells:

The light chain of anti-CD20 was inserted in a pCEP4 vector, identical to the vector used for the heavy chain, denoted pMGM01-CDC20 (pCEP4 InvitroGen). HEK293-F Freestyle™ cells (Invitrogen), cultured in 24-well plates were co-transfected with the vectors pMGM01-CD20 and pMGM05-CD20 (Fc-WT and variants) in equimolar amounts (250 ng/ml) with a Freestyle™ MAX reagent (1 µl/ml) following standard procedures (Invitrogen). The cells were cultured in suspension in a serum-free medium for 7 post-transfection days and the supernatants (1 ml) containing IgGs were harvested after centrifugation of the cells at 100 g for 10 min. The IgGs secreted in the supernatants were quantified using an ELISA assay on recombinant protein L (Pierce), with a purified anti-CD20 antibody produced in 293-F cells used as standard. The supernatants and standard antibodies diluted in series in PBS/0.05% Tween-20, were assayed on Maxisorp immunoplates (Nunc) previously coated with 0.25 µg protein L/well and blocked with 5 skim milk in PBS. After incubation for 1 hour at 37° C., the wells were washed three times with PBS/0.05% Tween-20. Binding of IgG variants was detected with a F(ab')2 fragment of goat anti-human IgG HRP (specific to the γ chain) (Sigma). The IgG variants produced were quantified (1-4 µg/ml) using the standard curve.

2.7. ELISA Assays on IgG Variants Produced in the Supernatants of 293-F Cells:

The IgG variants were assayed by ELISA for their binding to the human C1q complement and several human FcRs. Maxisorp immunoplates were coated with 0.5 µg C1q complement/well, 0.05 µg CD32aH/well, 0.2 µg CD16aF/well or 0.1 µg CD16aV/well in PBS. Immobilising nickel chelating plates (Nunc) were coated with 0.1 µg CD32aR/well or 0.4 µg CD32b/well in 0.01 M KCl. After coating overnight, at 4° C., the plates were washed twice with PBS/0.05% Tween-20 and saturated with PBS/4% BSA for 2 hours at 37° C. In parallel, the supernatants were diluted in PBS to a final concentration of 0.5 µg IgG/ml and mixed with F(ab')2 fragments of goat anti-human IgG HRP at the same concentration for 2 hours at ambient temperature. The IgGs aggregated to F(ab')2 were then incubated under gentle agitation for 1 hour at 30° C. on saturated ELISA plates without dilution for C1q, CD16aF, CD32aR and CD32b (i.e. IgG at 0.5 µg/ml), diluted in PBS at 0.25 µg/ml for CD16aV and CD32aH. The plates were then with detected with TMB (Pierce) and absorbance read at 450 nm.

Selections on the Mut3 Bank:

By means of this ELISA assay, the variants selected by phage display were assayed for their binding to the C1q complement and to the different receptors. They were assayed by comparison with the wild-type Fc (Fc-WT) and positive controls. 36 positive clones on CD16aV and/or C1q were thus selected on the Mut3 bank and used to construct the Mut4 bank.

Selections on the Mut4sel Bank:

ELISA assays performed on the 371 isolated clones allowed identification of 116 clones having a ratio higher than 2 for at least one FcγR and 17 clones with a ratio higher than 3 for C1q alone, which therefore corresponds to 133 clones of interest (Table 1).

TABLE 1

133 clones of interest isolated

| Name of mutant | Mutations | Results of ELISA assays | | | |
|---|---|---|---|---|---|
| | | C1q | CD16aV | CD32aR | CD32b |
| K3B-01 | N315D, N361H, P396L | 3.46 | 2.01 | 7.65 | 7.30 |
| A3A-105 | G316D, K326E | 5.18 | 2.48 | 4.50 | 7.13 |
| G3A-59 | N315D, T350A, P396L | 4.05 | 2.22 | 7.95 | 6.19 |
| J3B-81 | V284L, V323I, P352S, A378V, Y436H | 4.32 | 2.52 | 13.17 | 6.12 |
| J3A-123 | V266M, P352S, A378V | 0.77 | 0.35 | 7.76 | 5.93 |
| J3B-118 | P396L, N421T | 3.88 | 2.58 | 9.00 | 4.99 |
| A3A-46 | T350A, P396L | 2.19 | 2.40 | 6.17 | 4.79 |
| J3A-129 | T350A, G385R, P396L | 1.33 | 2.84 | 6.56 | 4.33 |
| QL4A-55 | N315D, P396L | 2.06 | 2.00 | 3.41 | 4.27 |
| A3A-27 | K326T, H435R | 5.81 | 2.21 | 3.41 | 4.10 |
| A3A-123 | N315D, P396L, K447N | 4.30 | 2.70 | 4.53 | 4.08 |
| J3A-109 | N315D, P396L, N434K | 1.75 | 2.46 | 6.01 | 4.07 |
| J3B-124 | P396L | 2.25 | 2.52 | 7.78 | 3.86 |
| A3A-79 | E283G, A378T, V397M | 1.62 | 1.35 | 3.07 | 3.83 |
| G3A-69 | K326T, V397M, F423L, A431V | 3.30 | 2.51 | 5.38 | 3.43 |
| A3A-178 | P396L, F423S | 4.03 | 1.73 | 3.55 | 3.37 |
| DS3A-39 | V284L, A378V | 2.76 | 3.18 | 3.48 | 3.30 |
| J3A-89 | V284L, N325S, A378V | 0.80 | 0.51 | 4.50 | 3.29 |
| DS3A-09 | A378V | 1.30 | 3.03 | 2.70 | 3.21 |
| J3A-120 | N315D, P343S, P396L | 1.66 | 2.32 | 4.71 | 3.16 |
| K3A-35 | K290E, S375R, F405V | 1.89 | 1.64 | 3.93 | 3.12 |
| DL3A-58 | S375R | 1.85 | 2.25 | 3.95 | 3.11 |
| A3A-50 | V284L, K322E, A378V | 0.67 | 1.50 | 5.08 | 3.10 |
| DL4A-146 | P352S, A378V | 1.56 | 2.31 | 2.35 | 3.10 |
| A3A-91 | K340E, A378V, N389S, N421T | 2.39 | 1.88 | 2.67 | 3.03 |
| DS3A-93 | F243I, P352S, A378V | 1.29 | 1.71 | 4.19 | 2.97 |
| A3A-184 | K334N, P352S, V397M | 1.44 | 2.90 | 3.06 | 2.91 |
| A3A-112 | T307P, N389T, V397M, S442F | 3.17 | 1.74 | 2.39 | 2.91 |
| A3A-132 | K248E, N315D, P396L | 5.03 | 2.12 | 3.70 | 2.79 |
| DS3B-92 | V284L, Y349H, A378V | 2.52 | 1.98 | 2.57 | 2.79 |
| QL3A-61 | N286I, A378V | 1.33 | 2.07 | 2.20 | 2.77 |
| J3B-115 | T359A, S383V, V397M | 1.72 | 1.69 | 5.17 | 2.77 |
| A3A-173 | K248E, K334R, A378V | OVER (>30) | 1.63 | 2.96 | 2.76 |
| A3A-164 | A378V, K447N | 1.64 | 2.41 | 2.82 | 2.71 |
| G3A-118 | N286I, P352S, A378V | 1.21 | 2.45 | 4.83 | 2.68 |
| QS5A-66 | T394P | 2.64 | 1.81 | 2.05 | 2.67 |
| DL4A-55 | A378V, N421T | 1.20 | 1.87 | 2.34 | 2.66 |
| G3A-176 | V259A, V284L, A378V, N421T | 1.05 | 1.68 | 2.10 | 2.61 |
| G3A-09 | A378T, V397M, K447N | 1.58 | 2.23 | 3.12 | 2.45 |
| DL3A-131 | A378T, V397M | 1.20 | 1.72 | 2.30 | 2.40 |
| J3A-10 | T307P, P396L | 5.18 | 2.74 | 5.71 | 2.39 |
| J3B-49 | N315D, T393A, P396L | 1.42 | 1.78 | 5.17 | 2.30 |
| K3A-41 | V302A, P352S, L398P | 1.11 | 0.77 | 2.17 | 2.30 |
| DL4A-54 | P352L, Q418P | 1.35 | 1.49 | 1.58 | 2.30 |
| A3A-06 | K248E, A378T, V397M | 4.79 | 1.59 | 1.78 | 2.29 |
| G3A-154 | A378T, V397M, F423P, S442P | 2.51 | 2.11 | 4.14 | 2.28 |
| A3A-12 | V363I, V397M | 3.02 | 1.56 | 2.99 | 2.27 |
| J3A-14 | K326T | 1.83 | 1.43 | 4.25 | 2.26 |
| G3A-05 | V323I, S383N | 2.21 | 1.33 | 3.37 | 2.25 |
| J3B-138 | K334R, T394P | 4.41 | 1.09 | 5.34 | 2.24 |
| QL2A-11 | V302A | 0.97 | 0.68 | 1.52 | 2.22 |
| K3B-32 | S254F, A378T, V397M | 5.80 | 1.42 | 3.72 | 2.22 |
| G3A-88 | K320E, T394P, G402D | 1.32 | 1.88 | 4.94 | 2.21 |
| K3B-30 | I253F, K326T, F423L, A431V | 7.34 | 1.58 | 5.99 | 2.20 |
| A3A-176 | V284A, A378V, A431T | 3.32 | 1.82 | 2.01 | 2.20 |
| K3A-59 | N315H, Y319H, V323I | 2.88 | 0.59 | 3.33 | 2.17 |
| J3B-120 | A378V, L398P | 1.29 | 1.67 | 2.94 | 2.17 |
| QL4B-10 | S383R, V397M | 1.40 | 1.35 | 1.95 | 2.08 |
| J3B-89 | K290E, V308I, A327T, S383N | 0.50 | 0.14 | 0.30 | 2.05 |
| G3A-83 | C226Y, A378V, N421T | 0.90 | 2.26 | 2.00 | 2.04 |
| G3A-165 | V323I, T393I | 1.33 | 1.52 | 4.15 | 2.04 |
| J3B-135 | K248E, S383R, V397M, N434S | 6.36 | 1.51 | 3.99 | 2.04 |
| A3A-137 | K290E, V323I, F405L | 1.91 | 1.65 | 3.02 | 2.03 |
| K3B-94 | R255W, A287T, P352S, A378V | 4.66 | 1.52 | 5.08 | 2.02 |
| A3A-30 | V284L, T350A | 2.09 | 1.47 | 2.47 | 2.01 |
| K3A-07 | N315D, A378V | 1.30 | 1.76 | 2.26 | 2.01 |
| G3A-164 | T394P, N434S | 1.72 | 1.19 | 2.29 | 1.99 |
| J3A-16 | N286Y, P352S, A378V | 1.46 | 1.83 | 3.54 | 1.98 |
| G3A-43 | A231V, A378V | 1.13 | 2.44 | 3.57 | 1.96 |
| A3A-09 | V308G, V323I | 3.65 | 1.23 | 2.26 | 1.95 |
| G3A-106 | S254F, V284L, A378V | 1.57 | 1.95 | 3.96 | 1.94 |
| J3A-08 | K274R, A378V, N421T | 1.17 | 1.53 | 3.47 | 1.94 |

TABLE 1-continued 133 clones of interest isolated

| Name of mutant | Mutations | Results of ELISA assays | | | |
|---|---|---|---|---|---|
| | | C1q | CD16aV | CD32aR | CD32b |
| QL3A-20 | V397M | 2.49 | 1.96 | 2.60 | 1.93 |
| G3A-108 | T394P, K414R | 1.50 | 1.54 | 3.67 | 1.91 |
| G3A-163 | V323I, M428T | 1.06 | 1.05 | 2.41 | 1.89 |
| A3A-125 | T394P, K447N | 1.94 | 1.83 | 2.48 | 1.84 |
| J3B-109 | E345G, V397M | 1.18 | 1.36 | 2.37 | 1.83 |
| DS3B-33 | K326T, F423L, A431V | 5.29 | 1.31 | 1.73 | 1.80 |
| QL4A-28 | F243L, P247T, Q362R, G402D, S440N | 0.74 | 1.65 | 2.88 | 1.80 |
| J3B-101 | Y278H, N315D, P396L | 1.18 | 1.64 | 2.35 | 1.78 |
| A3A-140 | D312G, A378T, V397M | 1.47 | 1.39 | 2.23 | 1.76 |
| G3A-25 | V262A, V305A, A378V | 1.76 | 1.56 | 2.01 | 1.70 |
| G3A-45 | K246R, A378V | 1.15 | 2.46 | 2.76 | 1.68 |
| QS6A-78 | V323I | 1.41 | 1.31 | 2.03 | 1.68 |
| K3B-91 | V308I, K326T, F423L, A431V | 4.84 | 1.13 | 2.71 | 1.65 |
| G3A-103 | K248E, A378V | 2.54 | 2.00 | 1.96 | 1.64 |
| G3A-07 | N276S, T394P, K439Q | 2.27 | 1.13 | 2.17 | 1.59 |
| A3A-17 | K290E, E380G | 1.64 | 2.02 | 1.91 | 1.59 |
| J3B-16 | S267G, A378T, V397M | 0.85 | 0.57 | 4.95 | 1.58 |
| J3B-23 | N286I, A378V, F423Y | 1.13 | 1.81 | 3.33 | 1.57 |
| J3B-68 | K320E, T350A | 0.82 | 1.57 | 3.30 | 1.55 |
| A3A-37 | A231T, K290E, S383N, F423L | 1.41 | 1.36 | 2.02 | 1.53 |
| J3A-49 | K320R, A378T, V397M | 0.60 | 0.45 | 2.15 | 1.52 |
| A3A-31 | K334R, L410R | 6.23 | 1.36 | 1.57 | 1.50 |
| A3A-41 | V323I, P352L, L398P | 2.00 | 1.46 | 2.53 | 1.47 |
| K3A-36 | K248E, K320M | 2.81 | 1.69 | 2.34 | 1.42 |
| J3A-06 | A378T, V397M, V412M | 1.60 | 1.65 | 2.74 | 1.41 |
| G3A-139 | T307N, V323I | 1.30 | 1.10 | 2.57 | 1.41 |
| G3A-98 | S375R, N434S | 1.14 | 1.56 | 3.02 | 1.40 |
| K3B-80 | V284L, T366A, A378V | 2.58 | 1.25 | 2.27 | 1.39 |
| J3B-74 | P230S, N389S, T394P | 0.94 | 0.65 | 1.81 | 1.39 |
| K3B-41 | Y349S, V397M | 1.82 | 1.27 | 2.11 | 1.38 |
| G3A-13 | K248E, A339T, T350A, S440N | 2.10 | 1.28 | 2.89 | 1.37 |
| J3B-44 | K246E, K274E, V397M | 1.59 | 1.05 | 2.38 | 1.37 |
| K3B-43 | A231P, K290E, S383N | 1.66 | 1.43 | 2.15 | 1.36 |
| J3B-107 | T307P, A378T, N389T | 1.50 | 1.32 | 2.05 | 1.36 |
| K3B-33 | K334R, K392R, S440G | 4.87 | 0.77 | 0.97 | 1.33 |
| K3A-11 | K246E, K290E, T307P, N389T | 1.73 | 1.65 | 2.00 | 1.33 |
| K3B-49 | D376G, S383R, V397M | 2.54 | 1.34 | 2.57 | 1.33 |
| G3A-95 | I336T, A378V | 1.05 | 2.25 | 1.82 | 1.31 |
| K3B-90 | V308A, K334R, A378V, K447N | 1.32 | 1.30 | 3.72 | 1.27 |
| A3A-146 | K290E, R355Q, S383N | 1.49 | 1.38 | 2.15 | 1.26 |
| A3A-11 | S254F, K447N | 4.78 | 1.18 | 1.02 | 1.22 |
| G3A-31 | K248E, K334Q | 3.60 | 1.52 | 1.06 | 1.21 |
| QL2A-16 | K248E, N421T | 5.30 | 0.79 | 0.77 | 1.19 |
| J3A-43 | K248E, P352L, Q418P | 2.96 | 1.23 | 2.13 | 1.19 |
| J3A-28 | E333G, A378T, V397M | 1.89 | 1.83 | 1.73 | 1.18 |
| A3A-07 | L365P, T366S, A378T | 1.20 | 1.94 | 1.17 | 1.18 |
| A3A-96 | K248E, L365P, A378T | 4.09 | 1.43 | 0.70 | 1.12 |
| K3B-87 | V323I, F405L | 1.56 | 0.93 | 2.36 | 1.10 |
| G3A-148 | K248E, S375R | 3.79 | 1.25 | 1.64 | 1.08 |
| K3B-34 | K334N, T394P, S408N, K414N | 0.62 | 1.18 | 2.25 | 1.02 |
| K3B-89 | L309M, A378V | 1.98 | 1.42 | 2.07 | 1.02 |
| G3A-49 | T307A, E380G | 3.66 | 0.91 | 0.82 | 1.02 |
| G3A-159 | E382G, L432P, Q438DEL | 3.00 | 0.91 | 1.13 | 0.98 |
| G3A-28 | T307P, H435R | 3.49 | 1.06 | 0.95 | 0.96 |
| K3B-78 | H310R, P352L, Q418P | 1.20 | 0.84 | 2.04 | 0.96 |
| G3A-22 | P352S, E382G, L432P, Y436N | 3.11 | 0.95 | 0.62 | 0.94 |
| G3A-56 | K248E, N421T, K447N | 3.25 | 0.71 | 1.03 | 0.89 |
| G3A-145 | E430G, K447N | 4.34 | 1.01 | 0.81 | 0.88 |
| A3A-21 | S267N, N384D, N389S, P396L | 4.32 | 1.00 | 0.56 | 0.88 |
| G3A-33 | K248E, S267N, I336M, P352L, P396L | 5.67 | 0.79 | 0.39 | 0.76 |
| G3A-51 | V240I, K246E, P353L | 3.90 | 0.95 | 0.51 | 0.64 |

Among these clones, 47 improved clones were used to construct the Mut5 bank. From these results, 18 new variants were constructed by directed mutagenesis so as to accumulate mutations of interest (Table 2).

TABLE 2

18 new variants constructed and compared with reference variants

| Name of mutant | Mutations | C1q | CD16aF | CD16aV | CD32aH | CD32aR | CD32b |
|---|---|---|---|---|---|---|---|
| A3A-105 | G316D, K326E | 5.18 | 1.31 | 2.48 | 1.50 | 4.50 | 7.13 |
| A3A-105A | G316D, K326E, T394P | 15.33 | 1.09 | 1.45 | 0.66 | 5.60 | 1.21 |
| A3A-105B | G316D, K326E, P396L | 14.30 | 2.25 | 3.52 | 3.92 | 12.64 | 4.16 |
| A3A-105C | G316D, K326E, V397M | 9.61 | 2.90 | 1.86 | 1.81 | 11.00 | 2.22 |
| A3A-105D | G316D, K326E, A378V | 13.32 | 2.46 | 3.68 | 1.39 | 8.20 | 5.96 |
| A3A-184 | K334N, P352S, V397M | 1.44 | 1.71 | 2.90 | 1.34 | 3.06 | 2.91 |
| A3A-184A | K334N, P352S, A378V, V397M | 1.75 | 3.40 | 4.74 | 3.25 | 5.03 | 2.32 |
| DS3A-09 | A378V | 1.30 | 3.15 | 3.03 | 2.90 | 2.70 | 3.21 |
| DS3A-09A | A378V, T394P | 1.24 | 2.29 | 2.83 | 2.26 | 2.00 | 1.26 |
| DS3A-09B | A378V, P396L | NA | 1.83 | 2.43 | NA | NA | NA |
| DS3A-09C | A378V, V397M | NA | 1.48 | 2.25 | NA | NA | NA |
| G3A-43 | A231V, A378V | 1.13 | 1.79 | 2.44 | 1.42 | 3.57 | 1.96 |
| G3A-43A | A231V, A378V, T394P | NA | 1.13 | 1.65 | NA | NA | NA |
| G3A-43B | A231V, A378V, P396L | NA | 1.85 | 2.42 | NA | NA | NA |
| G3A-43C | A231V, A378V, V397M | NA | 1.81 | 2.68 | NA | NA | NA |
| G3A-45 | K246R, A378V | 1.15 | 1.92 | 2.46 | 1.38 | 2.76 | 1.68 |
| G3A-45A | K246R, A378V, T394P | NA | 1.34 | 2.34 | NA | NA | NA |
| G3A-45B | K246R, A378V, P396L | NA | 1.37 | 1.75 | NA | NA | NA |
| G3A-45C | K246R, A378V, V397M | NA | 1.51 | 2.21 | NA | NA | NA |
| G3A-95 | I336T, A378V | 1.05 | 1.29 | 2.25 | 1.17 | 1.82 | 1.31 |
| G3A-95A | I336T, A378V, T394P | NA | 1.50 | 1.90 | NA | NA | NA |
| G3A-95B | I336T, A378V, P396L | NA | 2.00 | 2.54 | NA | NA | NA |
| G3A-95C | I336T, A378V, V397M | NA | 1.55 | 2.01 | NA | NA | NA |
| J3B-118 | P396L, N421T | 3.88 | 1.26 | 2.58 | NA | 9.00 | 4.99 |
| J3B-118A | A378V, P396L, N421T | NA | 1.76 | 3.37 | NA | NA | NA |
| QL3A-20 | V397M | 2.49 | 0.62 | 1.96 | 1.09 | 2.60 | 1.93 |
| QS5A-66 | T394P | 2.64 | NA | 1.81 | NA | 2.05 | 2.67 |

NA = Non-Determined

Finally, from these 151 assayed variants, 26 variants of interest were selected for production on a larger scale and more specific study (Table 3).

TABLE 3

26 selected new variants

| Name of mutant | Mutations | C1q | CD16aF | CD16aV | CD32aH | CD32aR | CD32b |
|---|---|---|---|---|---|---|---|
| A3A-105 | G316D, K326E | 5.18 | 1.31 | 2.48 | 1.50 | 4.50 | 7.13 |
| A3A-105D | G316D, K326E, A378V | 13.32 | 2.46 | 3.68 | 1.39 | 8.20 | 5.96 |
| A3A-14 | S298N, A378V | 0.53 | 0.96 | 0.85 | 0.22 | 0.35 | 0.88 |
| A3A-173 | K248E, K334R, A378V | NA | NA | 1.63 | NA | 2.96 | 2.76 |
| A3A-184 | K334N, P352S, V397M | 1.44 | 1.71 | 2.90 | 1.34 | 3.06 | 2.91 |
| A3A-184A | K334N, P352S, A378V, V397M | 1.75 | 3.40 | 4.74 | 3.25 | 5.03 | 2.32 |
| A3A-31 | K334R, L410R | 6.23 | NA | 1.36 | NA | 1.57 | 1.50 |
| DL4A-54 | P352L, Q418P | 1.35 | 1.18 | 1.49 | 1.09 | 1.58 | 2.30 |
| G3A-103 | K248E, A378V | 2.54 | 1.17 | 2.00 | 0.83 | 1.96 | 1.64 |
| G3A-139 | T307N, V323I | 1.30 | 0.81 | 1.10 | 0.65 | 2.57 | 1.41 |
| G3A-43 | A231V, A378V | 1.13 | 1.79 | 2.44 | 1.42 | 3.57 | 1.96 |
| G3A-45 | K246R, A378V | 1.15 | 1.92 | 2.46 | 1.38 | 2.76 | 1.68 |
| G3A-88 | K320E, T394P, G402D | 1.32 | NA | 1.88 | NA | 4.94 | 2.21 |

TABLE 3-continued 26 selected new variants

| Name of mutant | Mutations | Results of ELISA assays | | | | | |
|---|---|---|---|---|---|---|---|
| | | C1q | CD16aF | CD16aV | CD32aH | CD32aR | CD32b |
| G3A-95 | I336T, A378V | 1.05 | 1.29 | 2.25 | 1.17 | 1.82 | 1.31 |
| J3A-06 | A378T, V397M, V412M | 1.60 | 1.24 | 1.65 | 1.58 | 2.74 | 1.41 |
| J3A-14 | K326T | 1.83 | 0.52 | 1.43 | 0.99 | 4.25 | 2.26 |
| J3A-16 | N286Y, P352S, A378V | 1.46 | 1.35 | 1.83 | 1.77 | 3.54 | 1.98 |
| J3A-28 | E333G, A378T, V397M | 1.89 | 1.41 | 1.83 | 1.39 | 1.73 | 1.18 |
| J3A-115 | T359A, S383R, V397M | 1.72 | 1.32 | 1.69 | 1.42 | 5.17 | 2.77 |
| J3B-118 | P396L, N421T | 3.88 | 1.26 | 2.58 | NA | 9.00 | 4.99 |
| J3B-118A | A378V, P396L, N421T | NA | 1.76 | 3.37 | NA | NA | NA |
| J3B-16 | S267G, A378T, V397M | 0.85 | 0.59 | 0.57 | 0.42 | 4.95 | 1.58 |
| J3B-23 | N286I, A378V, F423Y | 1.13 | 1.91 | 1.81 | 1.57 | 3.33 | 1.57 |
| K3B-01 | N315D, N361H, P396L | 3.46 | 0.98 | 2.01 | 2.10 | 7.65 | 7.30 |
| K3B-90 | V308A, K334R, A378V, K447N | 1.32 | 1.06 | 1.30 | 1.40 | 3.72 | 1.27 |
| QL2A-16 | K248E, N421T | 5.30 | 0.69 | 0.79 | 0.33 | 0.77 | 1.19 |

NA = Non-Determined

Selections on the Mut5 Bank:

The ELISA assays performed on the 171 isolated clones allowed the identification of 87 clones with a ratio higher than 2 for at least one of the assayed FcγRs or C1q complement (Table 4).

TABLE 4

87 clones with a ratio higher than 2

| Name of mutant | Mutations | Results of ELISA assays | | | | | |
|---|---|---|---|---|---|---|---|
| | | C1q | CD16aF | CD16aV | CD32aH | CD32aR | CD32b |
| P3A-01 | K334N, S383R | 0.93 | 1.34 | 2.05 | 1.10 | 2.00 | 1.57 |
| P3A-17 | K334N, Y373D, A378V | 0.88 | 1.46 | 1.63 | 1.35 | 2.17 | 1.55 |
| P3A-18 | K248E, N286Y, K334R, A378V, K447N | 24.77 | 0.94 | 1.62 | 1.07 | 1.24 | 1.13 |
| P3A-23 | N361H, P396L | 2.70 | 1.75 | 2.49 | 2.53 | 3.33 | 1.76 |
| P3A-30 | K288E, K334N, P352S, V397M | 1.18 | 1.35 | 4.33 | 2.14 | 1.79 | 1.41 |
| P3A-31 | K248E, T359A, S383R, V397M | 5.80 | 0.80 | 2.05 | 1.80 | 1.62 | 1.51 |
| P3A-50 | T307P, A378V | 1.11 | 1.55 | 2.89 | 2.20 | 1.85 | 1.44 |
| P3A-56 | G316D | 1.74 | 1.07 | 1.90 | 2.02 | 1.45 | 1.39 |
| P3A-70 | K274R, A378V, V397M | 1.13 | 1.93 | 4.05 | 3.54 | 4.89 | 3.20 |
| P3A-74 | V302A, V397M | 0.92 | 0.72 | 0.63 | 1.47 | 2.43 | 1.32 |
| P3A-94 | L309P, T359A, S383R, V397M | 1.02 | 1.32 | 2.11 | 2.54 | 1.79 | 1.32 |
| N3A-111 | V302A, K334N, S375R | 1.36 | 0.82 | 1.18 | 1.20 | 2.73 | 2.33 |
| N3A-113 | E283G, Y349S, P396L | 6.55 | 1.30 | 1.73 | 2.17 | 5.19 | 2.94 |
| N3A-114 | K320E, S375R, F405V | 0.69 | 1.03 | 1.12 | 0.92 | 2.11 | 1.60 |
| N3A-117 | K334N | 1.32 | 1.61 | 2.28 | 1.31 | 1.93 | 1.98 |
| N3A-123 | K326E | 3.15 | 1.03 | 2.21 | 1.27 | 7.71 | 3.53 |
| N3A-132 | S375R, N389S | 1.71 | 0.99 | 1.10 | 1.41 | 3.50 | 2.35 |
| N3A-133 | K334N, P352S, K447N | 0.77 | 1.02 | 2.23 | 0.88 | 1.25 | 1.40 |
| N3A-138 | S298T, K334R, K370E | 3.56 | 0.90 | 0.68 | 0.59 | 0.73 | 1.17 |
| N3A-14 | T307N, A378V, K414R | 1.00 | 1.70 | 2.83 | 2.50 | 2.49 | 1.74 |
| N3A-141 | T350A, V379A, G385R, P396L | 2.82 | 1.30 | 1.79 | 2.36 | 5.60 | 5.70 |
| N3A-145 | S267G, K290E, E293G, E380G, V397M | 0.99 | 0.70 | 0.38 | 0.31 | 2.45 | 1.33 |
| N3A-150 | S267G, K334N, P352S, V397M | 0.86 | 0.76 | 0.68 | 0.33 | 4.82 | 1.78 |

TABLE 4-continued 87 clones with a ratio higher than 2

| Name of mutant | Mutations | \multicolumn{6}{c}{Results of ELISA assays} |
| | | C1q | CD16aF | CD16aV | CD32aH | CD32aR | CD32b |
|---|---|---|---|---|---|---|---|
| N3A-161 | K248E, N315D, A378V | 8.59 | 1.28 | 2.49 | 1.12 | 1.23 | 1.32 |
| N3A-175 | S375R, F405V | 0.94 | 1.16 | 2.47 | 1.99 | 1.30 | 1.10 |
| N3A-177 | V282A, K334R, T394P | 5.95 | 1.15 | 1.28 | 1.68 | 3.22 | 1.68 |
| N3A-190 | T307P, T394P | 2.46 | 1.35 | 2.46 | 2.93 | 3.33 | 1.94 |
| N3A-27 | K290E, A378V, K392R, S440G | 1.67 | 2.25 | 3.77 | 2.05 | 2.59 | 1.49 |
| N3A-28 | T366A, A378V | 1.04 | 1.77 | 2.89 | 2.26 | 1.84 | 1.36 |
| N3A-32 | K326T, K334N, P352S, N421T | 1.61 | 2.47 | 4.35 | 1.59 | 3.24 | 2.04 |
| N3A-52 | K326T, S383R, V397M | 3.70 | 1.11 | 2.07 | 1.92 | 5.40 | 2.41 |
| N3A-58 | V284L, K334R, A378V, K447N | 5.37 | 1.02 | 1.67 | 2.01 | 4.00 | 1.67 |
| N3A-59 | N315D, T366A, G385R, P396L | 1.08 | 1.25 | 1.66 | 1.75 | 2.73 | 1.56 |
| N3A-61 | V308A, K334R, A378V | 2.07 | 1.10 | 1.57 | 1.11 | 2.87 | 2.67 |
| N3A-74 | K288R, T394P | 1.38 | 1.22 | 1.51 | 1.58 | 2.15 | 1.73 |
| N3A-85 | K334R, V397M | 4.96 | 1.11 | 1.45 | 1.89 | 3.75 | 2.77 |
| N3A-87 | K290E, K320E, T350A, P396L | 0.91 | 2.15 | 2.85 | 3.12 | 5.94 | 4.63 |
| N3A-93 | A378T, P396L | 1.63 | 1.84 | 2.21 | 2.55 | 3.86 | 3.06 |
| O3A-04 | A231V, T359A, S383R, V397M | 1.00 | 1.16 | 1.21 | 1.69 | 2.35 | 1.09 |
| O3A-05 | K290E, T366A, A378V | 0.99 | 2.79 | 3.12 | 2.07 | 3.34 | 1.34 |
| O3A-10 | Y300H, T394P | 0.98 | 0.76 | 0.90 | 1.81 | 2.25 | 1.17 |
| O3A-11 | R255W, A287T, P352S, A378V, N421T | 1.85 | 1.01 | 2.10 | 2.20 | 3.15 | 1.5 |
| O3A-16 | K334R, A378V, K447N | 4.30 | 1.71 | 2.51 | 2.43 | 3.98 | 1.59 |
| O3A-17 | I336V, T359A, S383R, V397M | 0.85 | 1.79 | 2.70 | 2.30 | 1.73 | 0.93 |
| O3A-22 | K334R, P396L, H435R | 23.55 | 1.68 | 2.16 | 2.75 | 4.79 | 1.62 |
| O3A-24 | K326T, K447N | 2.12 | 1.23 | 2.27 | 1.55 | 2.94 | 1.40 |
| O3A-25 | V308A, K334R, A378T, V397M | 11.12 | 1.40 | 2.07 | 2.04 | 4.16 | 1.96 |
| O3A-34 | A231V, Y349S, V397M | 0.73 | 1.40 | 1.90 | 2.34 | 2.62 | 1.28 |
| O3A-38 | K248E, N286Y, Q418P | 2.17 | 1.59 | 1.16 | 0.99 | 0.69 | 0.57 |
| O3A-40 | V308A, A378T, V397M, V412M | 0.82 | 1.65 | 2.15 | 2.09 | 2.64 | 1.03 |
| O3A-42 | S304N, A378V | 1.04 | 2.16 | 0.53 | 0.87 | 0.87 | 1.77 |
| O3A-44 | A378V, K439R | 1.95 | 2.44 | 4.40 | 3.20 | 3.13 | 1.81 |
| O3A-45 | D270N, K334R, L410R | 3.32 | 1.57 | 0.61 | 0.56 | 1.19 | 1.36 |
| O3A-46 | V302A, A378V | 0.94 | 1.15 | 1.75 | 2.36 | 2.91 | 1.37 |
| O3A-50 | K334R, A378V, N421T | 3.62 | 1.28 | 2.49 | 2.15 | 4.02 | 2.30 |
| O3A-57 | T359A, V397M | 1.50 | 1.18 | 2.27 | 2.23 | 2.78 | 1.59 |
| O3A-66 | A378T, T394P | 1.10 | 1.42 | 2.42 | 2.36 | 2.45 | 1.76 |
| O3A-67 | K248E, N361H | 2.05 | 0.89 | 1.36 | 1.06 | 1.07 | 1.76 |
| O3A-69 | K290E, A378V | 1.44 | 2.64 | 4.04 | 2.62 | 4.11 | 2.06 |
| O3A-80 | K274R, T394P, G402D, K447N | 1.26 | 1.26 | 1.81 | 2.16 | 2.32 | 1.28 |
| O3A-81 | K274R, A378T, V397M | 1.36 | 1.20 | 2.39 | 2.06 | 3.08 | 1.58 |
| O3A-86 | K248E, K290E, N361H, P396L | 24.34 | 2.49 | 4.89 | 2.86 | 4.19 | 2.57 |
| O3A-93 | K290E, T394P | 2.07 | 1.45 | 3.53 | 2.54 | 3.36 | 1.78 |
| P4B-89 | T307P, T366A, A378V | 0.63 | 2.99 | 4.15 | 0.70 | 1.19 | 0.87 |
| Q4B-08 | V284L, K290E, A378V | 2.43 | 1.75 | 3.47 | 2.69 | 3.58 | 1.63 |
| Q4B-15 | K274R, A378V | 1.26 | 1.04 | 2.69 | 2.61 | 1.75 | 1.03 |
| Q4B-18 | I377T, A378V, F423Y | 1.21 | 1.08 | 2.82 | 1.96 | 1.37 | 1.07 |
| Q4B-34 | K248E, K290M, V308A, P352S | 4.47 | 0.63 | 0.56 | 0.38 | 0.70 | 0.75 |

TABLE 4-continued 87 clones with a ratio higher than 2

| Name of mutant | Mutations | \multicolumn{6}{c}{Results of ELISA assays} |
|---|---|---|---|---|---|---|---|
| | | C1q | CD16aF | CD16aV | CD32aH | CD32aR | CD32b |
| Q4B-59 | T350A, A378T, V397I | 1.32 | 2.22 | 2.01 | 2.76 | 2.52 | 1.51 |
| Q4B-61 | K320E, T394P, V397M | 0.87 | 1.10 | 0.98 | 1.60 | 2.43 | 1.08 |
| Q4B-68 | T307P, A378V, T394P | 3.33 | 1.53 | 4.12 | 4.01 | 3.69 | 1.03 |
| Q4B-91 | K334R, A378V | 2.81 | 1.14 | 2.35 | 2.61 | 2.46 | 0.94 |
| Q3A-01 | P352L, A378V | 1.13 | 1.14 | 1.53 | 2.04 | 1.81 | 0.87 |
| Q3A-39 | N286I, P396L, N421T | 2.80 | 1.63 | 1.99 | 3.52 | 3.09 | 1.02 |
| Q3A-58 | S267G, V397M | 0.73 | 1.30 | 0.34 | 0.40 | 2.87 | 1.02 |
| Q3A-85 | P396L, N421T, K447N | 3.80 | 1.65 | 2.17 | 3.67 | 3.50 | 1.13 |
| O3A-103 | K290E, K320T, A378V | 2.11 | 1.22 | 2.08 | 2.76 | 2.41 | 1.50 |
| O3A-117 | K334R, T394P, N421S | 0.98 | 1.05 | 1.71 | 2.29 | 3.05 | 1.37 |
| O3A-119 | K334N, V397M | 1.53 | 1.04 | 1.97 | 1.45 | 2.28 | 1.18 |
| O3A-126 | P227S, V284L, A378V | 4.58 | 1.31 | 2.93 | 2.85 | 4.47 | 1.29 |
| O3A-127 | V302A, K334R, T366A, S383R, V397M | 1.53 | 1.00 | 1.24 | 2.85 | 3.56 | 1.37 |
| O3A-131 | C261R, A378T, V397M, V412M | 2.25 | 1.03 | 1.72 | 2.00 | 2.27 | 1.15 |
| O3A-137 | K248E, T350A | 0.84 | 0.66 | 0.43 | 0.68 | 2.06 | 0.97 |
| O3A-172 | K320E, T394P | 8.19 | 0.88 | 1.46 | 2.01 | 2.52 | 1.06 |
| O3A-179 | R255Q, G385R | 0.81 | 0.74 | 0.83 | 0.57 | 2.86 | 1.30 |
| O3A-186 | T307P, V397M | 1.09 | 1.41 | 2.32 | 2.17 | 3.97 | 1.48 |
| O3A-99 | N276S, N286I, T359A, S383R, V397M | 2.14 | 1.32 | 2.27 | 2.84 | 3.09 | 1.42 |

Among these variants, 10 variants of interest were selected (Table 5).

TABLE 5

10 variants

| Name of mutant | Mutations | \multicolumn{6}{c}{Results of ELISA assays} |
|---|---|---|---|---|---|---|---|
| | | C1q | CD16aF | CD16aV | CD32aH | CD32aR | CD32b |
| O3A-05 | K290E, T366A, A378V | 0.99 | 2.79 | 3.12 | 2.07 | 3.34 | 1.34 |
| P4B-89 | T307P, T366A, A378V | 0.63 | 2.99 | 4.15 | 0.70 | 1.19 | 0.87 |
| O3A-86 | K248E, K290E, N361H, P396L | 24.34 | 2.49 | 4.89 | 2.86 | 4.19 | 2.57 |
| N3A-32 | K326T, K334N, P352S, N421T | 1.61 | 2.47 | 4.35 | 1.59 | 3.24 | 2.04 |
| O3A-44 | A378V, K439R | 1.95 | 2.44 | 4.40 | 3.20 | 3.13 | 1.81 |
| N3A-27 | K290E, A378V, K392R, S440G | 1.67 | 2.25 | 3.77 | 2.05 | 2.59 | 1.49 |
| N3A-87 | K290E, K320E, T350A, P396L | 0.91 | 2.15 | 2.85 | 3.12 | 5.94 | 4.63 |
| Q4B-68 | T307P, A378V, T394P | 3.33 | 1.53 | 4.12 | 4.01 | 3.69 | 1.03 |
| N3A-58 | V284L, K334R, A378V, K447N | 5.37 | 1.02 | 1.67 | 2.01 | 4.00 | 1.67 |
| Q3A-39 | N286I, P396L, N421T | 2.80 | 1.63 | 1.99 | 3.52 | 3.09 | 1.02 |

3. Production and Purification of Variants of Interest

The IgG variants were obtained by direct mutagenesis in pCEP4-WT-H-CD20. The IgG controls, i.e. C1, C3, C4, C5 and wild-type (WT), were produced with the G1m3 allotype (comprising 3 mutations compared with G1 m1, 17: (K214R/)D356E/L358M).

The 26 IgG variants derived from the Mut4sel bank, and the wild-type, were produced with the G1 m1, 17 allotype. They were produced by incubation for 6-7 days in batches (250-300 ml) of 293-E cells (Freestyle Invitrogen) in F17 medium.

Centrifugation and filtration were then carried out.

Purification was performed on Protein A Hi-Trap, and elution with a 25 mM citrate buffer, pH=3.0, neutralisation and dialysis in TBS or PBS before sterilisation.

10 mg of each IgG control, i.e. C1, C3, C4, C5 and wild-type (WTG1m3 and WTG1 m1, 17) were obtained, and 2-3 mg of 26 IgG variants.

Their characterization shows that the molecular weight is maintained and that glycosylation profiles are similar for all variants.

4. Assays of Variants of Interest 4.1. Binding Assays on FcRn

Jurkat-FcRn cells were incubated at pH=6.0 with the IgG variants at different concentrations (0 to 1000 µg/ml) and with Rituximab-Alexa.

Flow cytometry was conducted on the bound Rituximab-Alexa.

The results do not show any loss of binding to FcRn for all IgG variants.

4.2 Binding Assays to the Antigen

Raji cells were incubated with the IgG variants at 1 µg/ml for 15 minutes at 4° C.

The bound IgGs were detected by binding with a PE anti-human IgG secondary antibody (for 15 minutes at 4° C.).

The results show that recognition of the antigen is not deteriorated by the different mutations on the Fc.

All the IgG variants were bound to CD20 on the cells, similar to the IgG-WT control.

4.3 ELISA Binding Assays to CD16aV/F

The purified antibodies were assayed with ELISA for binding to CD16F and CD16aV following the same protocol as described under item 2.6, diluting the antibodies to different concentrations.

4.4. ADCC Activity Assays

NK cells were incubated with target Raji cells expressing CD20, in the presence of different concentrations of IgG variants (0.005 to 5000 ng/ml).

The level of intracellular LDH released by the lysed target cells was measured.

Human NK cells were purified from the peripheral blood of healthy volunteer donors using the negative depletion technique developed by Miltenyi. The ADCC assay comprised the incubation of NK cells with target Raji cells expressing the CD20 antigen, in the presence of different concentrations of anti-CD20 antibodies. After an incubation time of 16 hours, the cytotoxicity induced by the anti-CD20 antibodies was measured by quantifying intracellular lactate dehydrogenase (LDH) in the cell supernatants. The results of specific lysis are expressed as a lysis percentage as a function of antibody concentration. The EC50 value (antibody concentration inducing 50% of the maximum lysis induced by IgG-WT) and Emax value (percentage maximum lysis) were calculated using the software GraphPad PRISM.

The results are given in Tables 6 and 7.

TABLE 6

Results of ADCC assays

| Mutant | G3A43 | G3A45 | J3B-118 | J3B16 | A3A-184 | WT |
|---|---|---|---|---|---|---|
| EC50: Antibody concentration (ng/ml) giving 50% lysis of an internal control | 1.03 | 4.38 | 1.27 | >5545.36 | 2.35 | 12.34 |
| Ratio [WT]/[antibody] | 11.98 | 2.82 | 9.72 | <0.0022 | 5.25 | 1 |

TABLE 7a

Results of ADCC assays

| Mutant | EC50: Antibody concentration (ng/ml) giving 50% maximum lysis of an internal control | Ratio [WT]/[antibody] |
|---|---|---|
| G3A-103 | 0.31 | 33.90 |
| A3A-184A | 0.34 | 30.91 |
| J3B-23 | 0.57 | 18.44 |
| J3A-28 | 0.57 | 18.44 |
| K3B-01 | 0.69 | 15.23 |
| A3A-14 | 0.82 | 12.82 |
| G3A-95 | 0.97 | 10.84 |
| J3B-118A | 0.97 | 10.84 |
| J3A-16 | 1.27 | 8.28 |
| J3A-06 | 1.27 | 8.28 |
| A3A-105D | 1.27 | 8.28 |
| G3A-139 | 2.80 | 3.75 |
| QL2A-16 | 4.36 | 2.41 |
| J3A-14 | 7.39 | 1.42 |
| G3A-88 | 8.07 | 1.30 |
| WT | 10.51 | 1 |
| K3B-87 | 16.33 | 0.64 |
| DL4A-54 | >5000 | <0.002 |
| A3A-90 | >5000 | <0.002 |
| A3A-34 | >5000 | <0.002 |

TABLE 7b

Results of ADCC assays

| Mutant | EC50: Antibody concentration (ng/ml) giving 50% maximum lysis of an internal control | Ratio [WT]/[antibody] |
|---|---|---|
| WT | 0.45 | 1 |
| A3A-173 | 1.38 | 0.33 |
| K3B-90 | 0.75 | 0.60 |
| A3A-105 | 1.374 | 0.33 |
| A3A-31 | 1.839 | 0.24 |
| J3B-115 | 0.57 | 0.79 |

TABLE 7c

Results of ADCC assays (EC45 instead of EC50)

| Mutant | EC45: Antibody concentration (ng/ml) giving 45% maximum lysis of an internal control | Ratio [WT]/[antibody] |
|---|---|---|
| WT | 1.60 | 1 |
| O3A-44 | 2.6 | 0.62 |
| N3A-27 | 18.7 | 0.86 |
| N3A-58 | 4.4 | 0.36 |
| O3A-86 | 4.4 | 0.36 |
| N3A-87 | 1.0 | 1 |
| P4B-89 | 3.6 | 0.44 |
| O3A-05 | 0.2 | 8 |
| N3A-32 | 2.9 | 0.55 |
| Q3A-39 | 0.3 | 5.33 |
| Q4B-68 | 1.7 | 0.94 |

The best variants are A3A-184A et G3A-103.

4.5. CDC Activity Assays

Target Raji cells expressing the CD20 antigen were incubated with different concentrations of anti-CD20 antibodies (0 to 5000 ng/ml) in the presence of rabbit serum as complement source (Cedarlane, 1/10 dilution). After an incubation time of 1 hour at 37° C., the level of LDH released into the supernatant by the lysed target cells was measured chromogenically (cytotoxicity detection kit by Roche Applied Sciences) and used to quantify antibody-mediated complement-dependent cytotoxicity. The results are expressed as percent lysis. EC50 (number of antibodies inducing 50% maximum lysis) and Emax (percent maximum lysis) were calculated using the software GraphPad PRISM.

The results are given in Tables 8 and 9.

TABLE 8

Results of CDC assays

| Antibody | Antibody concentration (ng/ml) giving 50% lysis of an internal control | Ratio [WT]/[antibody] |
|---|---|---|
| A3A-173 | 16.01 | 16.36 |
| K3B-90 | 23.12 | 11.33 |
| J3B-118 | 38.69 | 6.77 |
| A3A-105 | 64.76 | 4.05 |
| A3A-31 | 108.37 | 2.42 |
| J3B-115 | 145.44 | 1.80 |
| G3A-43 | 168.49 | 1.55 |
| G3A-45 | 195.20 | 1.34 |
| A3A-184 | 210.10 | 1.25 |
| J3B-16 | 210.10 | 1.25 |
| WT | 261.97 | 1 |

TABLE 9a

Results of CDC assays

| Antibody | Antibody concentration (ng/ml) giving 50% lysis of an internal control | Ratio [WT]/[antibody] |
|---|---|---|
| J3B-118A | 21.564 | 10.98 |
| J3A-28 | 31.004 | 7.64 |
| G3A-103 | 33.339 | 7.10 |
| A3A-105D | 38.550 | 6.14 |
| QL2A-16 | 51.544 | 4.59 |
| K3B-01 | 59.600 | 3.97 |

TABLE 9a-continued

Results of CDC assays

| Antibody | Antibody concentration (ng/ml) giving 50% lysis of an internal control | Ratio [WT]/[antibody] |
|---|---|---|
| J3A-06 | 64.089 | 6.70 |
| J3A-14 | 64.089 | 6.70 |
| A3A-184A | 74.107 | 3.20 |
| G3A-139 | 85.691 | 2.76 |
| J3B-23 | 99.085 | 2.39 |
| K3B-87 | 106.548 | 2.22 |
| A3A-34 | 123.202 | 1.92 |
| J3A-16 | 132.481 | 1.79 |
| DL4A-54 | 164.727 | 1.44 |
| G3A-95 | 177.134 | 1.34 |
| WT | 236.837 | 1 |
| G3A-88 | 273.856 | 0.86 |
| A3A-14 | 340.513 | 0.70 |
| A3A-90 | 566.098 | 0.42 |

TABLE 9b

Results of CDC assays

| Antibody | Antibody concentration (ng/ml) giving 50% lysis of an internal control | Ratio [WT]/[antibody] |
|---|---|---|
| WT | 133 | 1 |
| O3A-44 | 129 | 1.03 |
| N3A-27 | 179 | 0.74 |
| N3A-58 | 36 | 3.69 |
| O3A-86 | 44 | 3.02 |
| N3A-87 | 106 | 1.25 |
| P4B-89 | 115 | 1.16 |
| O3A-05 | 91 | 1.46 |
| N3A-32 | 66 | 2.02 |
| Q3A-39 | 61 | 2.18 |
| Q4B-68 | 126 | 1.06 |

Table 10 below gives the results obtained with some variants classified into sub-groups.

TABLE 10

| Name | Mutations | ADCC | CDC | ELISA ratio (purified antibodies) | | | |
|---|---|---|---|---|---|---|---|
| | | | | CD32aH | CD32aR | CD32b | CD64 |
| G3A-103 | K248E, A378V | 33.9 | 7.1 | 0.5 | 0.9 | 1.2 | 1.2 |
| J3A-28 | E333G, A378T, V397M | 18.4 | 7.6 | 1.1 | 1.3 | 1.6 | 1.3 |
| J3B-118A | P396L, N421T, A378V | 10.8 | 11.0 | 2.7 | 1.8 | 3.7 | 1.4 |
| J3B-118 | P396L, N421T | 9.7 | 12.2 | 1.0 | 1.1 | 1.0 | 1.6 |
| A3A-105D | G316D, K326E, A378V | 8.3 | 6.1 | 1.4 | 2.6 | 2.0 | 1.5 |
| A3A-14 | S298N, A378V | 12.8 | 0.7 | 1.1 | 0.8 | 0.9 | 1.6 |
| G3A-95 | I336T, A378V | 10.8 | 1.3 | 0.7 | 0.9 | 1.0 | 1.3 |
| A3A-184A | K334N, P352S, V397M, A378V | 30.9 | 3.2 | 1.3 | 4.3 | 3.1 | 1.5 |
| J3B-23 | N286I, A378V, F423Y | 18.4 | 2.4 | ND | ND | ND | ND |
| K3B-01 | N315D, N361H, P396L | 15.2 | 4.0 | 5.7 | 1.0 | 1.0 | 2.3 |
| G3A-43 | A231V, A378V | 12.0 | 2.8 | 5.3 | 3.6 | 2.7 | 1.4 |
| J3A-06 | A378T, V397M, V412M | 8.3 | 3.7 | 0.84 | 2.0 | 2.4 | 1.3 |
| J3A-16 | N286Y, P352S, A378V | 8.3 | 1.8 | 2.61 | 1.7 | 1.7 | 1.3 |
| O3A-05 | K290E, T366A, A378V | 8.0 | 1.5 | 4.02 | 3.3 | 4.5 | 1.2 |
| Q3A-39 | N286I, P396L, N421T | 5.3 | 2.2 | 4.83 | 2.3 | 3.8 | 1.5 |
| A3A-184 | K334N, P352S, V397M | 5.3 | 2.2 | 1.33 | 3.2 | 3.3 | 1.4 |
| K3B-90 | V308A, K334R, A378V, K447N | 0.6 | 20.4 | 1.20 | 1.2 | 1.1 | 1.5 |
| A3A-173 | K248E, K334R, A378V | 0.3 | 29.5 | 0.95 | 1.3 | 1.3 | 1.2 |
| J3A-14 | K326T | 1.4 | 3.7 | 1.86 | 1.3 | 1.5 | 2.3 |
| G3A-88 | K320E, T394P, G402D | 1.3 | 0.9 | 2.94 | 3.7 | 3.9 | 2.4 |
| N3A-87 | K290E, K320E, T350A, P396L | 1.0 | 1.3 | 3.92 | 3.7 | 9.0 | 1.5 |
| J3B-115 | T359A, S383R, V397M | 0.8 | 3.2 | 4.65 | 5.1 | 4.2 | 1.5 |

Following Table 11 gives some possible variants of the invention:

TABLE 11

| Name | Mutations | Starting variant | Added mutation |
|---|---|---|---|
| G3A-95D | S298N, I336T, A378V | G3A-95 | S298N |
| K3B-90A | K248E, V308A, K334R, A378V, K447N | K3B-90 | K248E |
| G3A-88A | K320E, K326T, T394P, G402D | G3A-88 | K326T |
| N3A-87A | K290E, K320E, K326T, T350A, P396L | N3A-87 | K326T |
| A3A-105E | K248E, G316D, K326E, A378V | A3A-105D | K248E |
| A3A-14A | K248E, S298N, A378V | A3A-14 | K248E |
| A3A-184B | K248E, K334N, P352S, V397M, A378V | A3A-184 | K248E |
| G3A-43D | K248E, A231V, A378V | G3A-43 | K248E |
| G3A-95E | K248E, I336T, A378V | G3A-95 | K248E |
| J3A-28A | K248E, E333G, A378T, V397M | J3A-28 | K248E |
| J3B-118B | K248E, P396L, N421T, A378V | J3B-118A | K248E |
| J3B-23A | N286I, A378V, F423Y | J3B-23 | K248E |
| K3B-01A | N315D, N361H, P396L | K3B-01 | K248E |
| A3A-105F | G316D, K326E, E333G, A378V | A3A-105 | E333G |
| A3A-14B | S298N, E333G, A378V | A3A-14 | E333G |
| A3A-184C | E333G, K334N, P352S, V397M, A378V | A3A-184 | E333G |
| G3A-103A | K248E, E333G, A378V | G3A-103 | E333G |
| G3A-43E | A231V, E333G, A378V | G3A-43 | E333G |
| G3A-95F | E333G, I336T, A378V | G3A-95 | E333G |
| J3B-118C | E333G, P396L, N421T, A378V | J3B-118 | E333G |
| J3B-23B | N286I, E333G, A378V, F423Y | J3B-23 | E333G |
| K3B-01B | N315D, E333G, N361H, P396L | K3B-01 | E333G |
| A3A-105G | G316D, K326E, A378V, F423Y | A3A-105 | F423Y |
| A3A-14C | E333G, S298N, A378V, F423Y | A3A-14 | F423Y |
| A3A-184D | K334N, P352S, V397M, A378V, F423Y | A3A-184 | F423Y |
| G3A-103B | K248E, A378V, F423Y | G3A-103 | F423Y |
| G3A-43F | A231V, A378V, F423Y | G3A-43 | F423Y |
| G3A-95G | I336T, A378V, F423Y | G3A-95 | F423Y |
| J3A-28B | E333G, A378T, V397M, F423Y | J3A-28 | F423Y |
| J3B-118D | P396L, N421T, A378V, F423Y | J3B-118 | F423Y |
| K3B-01C | N315D, N361H, P396L, F423Y | K3B-01 | F423Y |

The invention claimed is:

1. A polypeptide comprising a mutated Fc region that has a functional activity mediated by the Fc region that is increased by a ratio of at least 15 compared to a parent polypeptide, wherein said functional activity mediated by the Fc region is selected from among antibody-dependent cell cytotoxicity (ADCC) and complement-dependent cytotoxicity (CDC), wherein the parent polypeptide comprises a Fc region of SEQ ID NO:1, and wherein said mutated Fc region has been modified by a combination of the mutations selected from:

(i) 248E and 378V;
(ii) 334N, 352S, 397M and 378V,
(iii) 286I, 378V and 423Y, and
(iv) 248E, 334R and 378V, compared to SEQ ID NO:1, and wherein said mutated Fc region optionally has a maximum of two further mutations in SEQ ID NO:1, wherein one of them is on position 434, the numbering being that of the EU Index or Kabat equivalent.

2. The polypeptide according to claim 1, having functional activity mediated by the Fc region that is increased compared with that of the parent polypeptide by a ratio of higher than 20.

3. The polypeptide according to claim 1, wherein said mutated Fc region has an increased affinity for at least one of the receptors (FcRs) of the Fc region selected from among the C1q complement and FcgRIIIa (CD16a), FcgRIIa (CD32a) and FcgRIIb (CD32b) receptors.

4. A polypeptide comprising a mutated Fc region that has a functional activity mediated by the Fc region that is increased by a ratio of at least 15 compared to a parent polypeptide, wherein said functional activity mediated by the Fc region is selected from among antibody-dependent cell cytotoxicity (ADCC) and complement-dependent cytotoxicity (CDC), wherein the parent polypeptide comprises a Fc region of SEQ ID NO:1, and wherein the mutated Fc region has only been mutated at a combination of positions selected from:
- 248E and 378V;
- 334N, 352S, 397M and 378V,
- 286I, 378V and 423Y, and
- 248E, 334R and 378V,
- compared to SEQ ID NO:1,
  the numbering being that of the EU Index or Kabat equivalent.

5. The polypeptide according to claim 1, wherein the polypeptide is selected from among an isolated Fc region, a sequence derived from an isolated Fc region, an antibody and a fusion protein comprising an Fc region.

6. The polypeptide according to claim 1, wherein the polypeptide consists of an Fc region or consists of an antibody.

7. The polypeptide according to claim 1, wherein the polypeptide is produced in the milk of transgenic animals.

8. A composition of polypeptides according to claim 1, wherein the purified polypeptides of said composition, on their Asn297 glycosylation site, have N-glycans with a fucosylation rate lower than 65%.

9. The composition of polypeptides according to claim 8, wherein the purified polypeptides of said composition, on their Asn297 glycosylation site, have a glycan structure of biantennary type with short chains, low sialylation, having non-intercalary terminal mannoses and/or terminal N-acetylglucosamines.

10. The composition of polypeptides according to claim 9, wherein the purified polypeptides of said composition have a content higher than 60% for the G0+G1+G0F+G1F forms, the G0F+G1F forms being lower than 50%.

11. The composition of polypeptides according to claim 9, wherein the purified polypeptides of said composition have a content higher than 60% for the G0+G1+G0F+G1F forms, the fucose content being lower than 65%.

12. A pharmaceutical composition comprising (i) a polypeptide according to claim 1, and (ii) at least one pharmaceutically acceptable excipient.

13. The polypeptide according to claim 6, wherein the polypeptide is an antibody directed against an antigen selected from among a tumour antigen, viral antigen, bacterial antigen, fungal antigen, a toxin, membrane-bound or circulating membrane, a membrane receptor.

14. A method to produce a polypeptide comprising an Fc region and having functional activity, mediated by the Fc region, that is increased compared with that of a parent polypeptide by a ratio of at least 15, wherein said functional activity mediated by the Fc region is selected from among antibody-dependent cell cytotoxicity (ADCC), complement-dependent cytotoxicity (CDC) and a combination of these activities, wherein the parent polypeptide comprises a Fc region of SEQ ID NO:1, said method comprising a step to introduce a combination of the following mutations, said combination being selected from among:
  (i) the combination of mutations 248E and 378V;
  (ii) the combination of mutations 334N, 352S, 397M and 378V,
  (iii) the combination of mutations 286I, 378V and 423Y, or
  (iv) the combination of mutations 248E, 334R and 378V,
  and optionally 2 further mutations wherein one of them is on position 434, the numbering being that of the EU Index or Kabat equivalent.

15. The method according to claim 14, wherein it comprises a step to introduce a combination of the following mutations, said combination being selected from among:
- 248E and 378V;
- 334N, 352S, 397M and 378V,
- 286I, 378V and 423Y, or
- 248E, 334R and 378V,
  the numbering being that of the EU Index or Kabat equivalent.

16. The polypeptide according to claim 4, wherein the polypeptide is selected from among an isolated Fc region, a sequence derived from an isolated Fc region, an antibody and a fusion protein comprising an Fc region.

17. The polypeptide according to claim 4, wherein the polypeptide consists of an Fc region or consists of an antibody.

18. The polypeptide according to claim 4, wherein the polypeptide is produced in the milk of transgenic animals.

19. A composition of polypeptides according to claim 4, wherein the purified polypeptides of said composition, on their Asn297 glycosylation site, have N-glycans with a fucosylation rate lower than 65%.

20. The composition of polypeptides according to claim 19, wherein the purified polypeptides of said composition, on their Asn297 glycosylation site, have a glycan structure of biantennary type with short chains, low sialylation, having non-intercalary terminal mannoses and/or terminal N-acetylglucosamines.

21. The composition of polypeptides according to claim 20, wherein the purified polypeptides of said composition have a content higher than 60% for the G0+G1+G0F+G1F forms, the G0F+G1F forms being lower than 50%.

22. The composition of polypeptides according to claim 20, wherein the purified polypeptides of said composition have a content higher than 60% for the G0+G1+G0F+G1F forms, the fucose content being lower than 65%.

23. A pharmaceutical composition comprising (i) a polypeptide according to claim 4, and (ii) at least one pharmaceutically acceptable excipient.

24. The polypeptide according to claim 16, wherein the polypeptide is an antibody directed against an antigen selected from among a tumour antigen, viral antigen, bacterial antigen, fungal antigen, a toxin, membrane-bound or circulating membrane, a membrane receptor.

* * * * *

SEQUENCE LISTING

<160> NUMBER OF SEQ ID NOS: 12

<210> SEQ ID NO 1
<211> LENGTH: 222
<212> TYPE: PRT
<213> ORGANISM: Artificial Sequence
<220> FEATURE:
<223> OTHER INFORMATION: Fc of IgG1 G1m1,17

<400> SEQUENCE: 1

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
        50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val

```
            130                 135                 140
Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Val Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Val Phe Ser Cys Ser Val Met His Glu Ala Leu His
                195                 200                 205

Asn His Tyr Thr Gln Lys Ser Leu Ser Leu Ser Pro Gly Lys
                210                 215                 220

<210> SEQ ID NO 2
<211> LENGTH: 221
<212> TYPE: PRT
<213> ORGANISM: Artificial Sequence
<220> FEATURE:
<223> OTHER INFORMATION: Fc of IgG2

<400> SEQUENCE: 2

Cys Pro Pro Cys Pro Ala Pro Pro Val Ala Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser His Glu Asp Pro Glu Val Gln
                35                  40                  45

Phe Asn Trp Tyr Val Asp Gly Val Glu Val His Asn Ala Lys Thr Lys
50                  55                  60

Pro Arg Glu Glu Gln Phe Asn Ser Thr Phe Arg Val Val Ser Val Leu
65                  70                  75                  80

Thr Val Val His Gln Asp Trp Leu Asn Gly Lys Glu Tyr Lys Cys Lys
                85                  90                  95

Val Ser Asn Lys Gly Leu Pro Ala Pro Ile Glu Lys Thr Ile Ser Lys
                100                 105                 110

Thr Lys Gly Gln Pro Arg Glu Pro Gln Val Tyr Thr Leu Pro Pro Ser
                115                 120                 125

Arg Glu Glu Met Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Met Leu Asp Ser Asp Gly
                165                 170                 175

Ser Phe Phe Leu Tyr Ser Lys Leu Thr Val Asp Lys Ser Arg Trp Gln
                180                 185                 190

Gln Gly Asn Val Phe Ser Cys Ser Val Met His Glu Ala Leu His Asn
                195                 200                 205

His Tyr Thr Gln Lys Ser Leu Ser Leu Ser Pro Gly Lys
                210                 215                 220

<210> SEQ ID NO 3
<211> LENGTH: 222
<212> TYPE: PRT
<213> ORGANISM: Artificial Sequence
<220> FEATURE:
<223> OTHER INFORMATION: Fc of IgG3

<400> SEQUENCE: 3
```

Cys Pro Arg Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Gln Phe Lys Trp Tyr Val Asp Gly Val Glu Val His Asn Ala Lys Thr
    50                  55                  60

Lys Pro Arg Glu Glu Gln Tyr Asn Ser Thr Phe Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
                100                 105                 110

Lys Thr Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
        130                 135                 140

Lys Gly Phe Tyr Pro Ser Asp Ile Ala Val Glu Trp Glu Ser Ser Gly
145                 150                 155                 160

Gln Pro Glu Asn Asn Tyr Asn Thr Thr Pro Pro Met Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Ile Phe Ser Cys Ser Val Met His Glu Ala Leu His
            195                 200                 205

Asn Arg Phe Thr Gln Lys Ser Leu Ser Leu Ser Pro Gly Lys
        210                 215                 220

<210> SEQ ID NO 4
<211> LENGTH: 222
<212> TYPE: PRT
<213> ORGANISM: Artificial Sequence
<220> FEATURE:
<223> OTHER INFORMATION: Fc of IgG4

<400> SEQUENCE: 4

Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
            35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Gln Glu Glu Met Thr Lys Asn Gln Val Ser Leu Thr Cys Leu Val
        130                 135                 140

```
Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220
```

<210> SEQ ID NO 5
<211> LENGTH: 222
<212> TYPE: PRT
<213> ORGANISM: Artificial Sequence
<220> FEATURE:
<223> OTHER INFORMATION: Fc of IgG1 G1m3

<400> SEQUENCE: 5

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 6
<211> LENGTH: 232
<212> TYPE: PRT
<213> ORGANISM: Artificial Sequence
<220> FEATURE:
<223> OTHER INFORMATION: Fc of IgG1 G1m1,17

<400> SEQUENCE: 6

```
Glu Pro Lys Ser Cys Asp Lys Thr His Thr Cys Pro Pro Cys Pro Ala
1               5                   10                  15
```

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
             85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
             165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 7
<211> LENGTH: 228
<212> TYPE: PRT
<213> ORGANISM: Artificial Sequence
<220> FEATURE:
<223> OTHER INFORMATION: Fc of IgG2

<400> SEQUENCE: 7

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val His Gln Asp Trp Leu Asn
             85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
130                 135                 140
```

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 8
<211> LENGTH: 279
<212> TYPE: PRT
<213> ORGANISM: Artificial Sequence
<220> FEATURE:
<223> OTHER INFORMATION: Fc of IgG3

<400> SEQUENCE: 8

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270
```

```
Leu Ser Leu Ser Pro Gly Lys
        275

<210> SEQ ID NO 9
<211> LENGTH: 229
<212> TYPE: PRT
<213> ORGANISM: Artificial Sequence
<220> FEATURE:
<223> OTHER INFORMATION: Fc of IgG4

<400> SEQUENCE: 9

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 10
<211> LENGTH: 232
<212> TYPE: PRT
<213> ORGANISM: Artificial Sequence
<220> FEATURE:
<223> OTHER INFORMATION: Fc of IgG1 G1m3

<400> SEQUENCE: 10

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
```

```
                50                   55                   60
Asp Gly Val Glu Val His Asn Ala Lys Thr Lys Pro Arg Glu Glu Gln
65                   70                   75                   80

Tyr Asn Ser Thr Tyr Arg Val Val Ser Val Leu Thr Val Leu His Gln
                85                   90                   95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 11
<211> LENGTH: 35
<212> TYPE: DNA
<213> ORGANISM: Artificial Sequence
<220> FEATURE:
<223> OTHER INFORMATION: primer MG_619

<400> SEQUENCE: 11
agtactgact ctacctagga tcctgcccac cgtgc                               35

<210> SEQ ID NO 12
<211> LENGTH: 35
<212> TYPE: DNA
<213> ORGANISM: Artificial Sequence
<220> FEATURE:
<223> OTHER INFORMATION: primer MG_621

<400> SEQUENCE: 12
actgctcgat gtccgtacta tgcggccgcg aattc                               35
```

UNITED STATES PATENT AND TRADEMARK OFFICE
CERTIFICATE OF CORRECTION

| | |
|---|---|
| PATENT NO. | : 11,649,271 B2 |
| APPLICATION NO. | : 15/554022 |
| DATED | : May 16, 2023 |
| INVENTOR(S) | : Celine Monnet et al. |

It is certified that error appears in the above-identified patent and that said Letters Patent is hereby corrected as shown below:

On the Title Page

Please amend Item (73) to read as follows:
--(73) Assignee: LABORATOIRE FRANÇAIS DU FRACTIONNEMENT ET DES BIOTECHNOLOGIES, Puteaux, (FR)--.

Signed and Sealed this
Fourth Day of July, 2023

Katherine Kelly Vidal
*Director of the United States Patent and Trademark Office*